US008951805B2

(12) United States Patent
Fritchie et al.

(10) Patent No.: US 8,951,805 B2
(45) Date of Patent: Feb. 10, 2015

(54) SYSTEM FOR MANAGING INVENTORY OF BULK LIQUIDS

(71) Applicant: Abbott Laboratories, Abbott Park, IL (US)

(72) Inventors: Patrick P. Fritchie, Southlake, TX (US); Gregory E. Gardner, Grapevine, TX (US); Richard W. Mahoney, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/247,887

(22) Filed: Apr. 8, 2014

(65) Prior Publication Data

US 2014/0234181 A1 Aug. 21, 2014

Related U.S. Application Data

(63) Continuation of application No. 12/487,716, filed on Jun. 19, 2009, now Pat. No. 8,715,574.

(51) Int. Cl.
*G01N 15/06* (2006.01)
*G01N 33/00* (2006.01)
(Continued)

(52) U.S. Cl.
CPC .............. *G01N 1/28* (2013.01); *G01N 35/1009* (2013.01); *G01N 35/1065* (2013.01); *G01N 35/1074* (2013.01); *G01N 2035/1025* (2013.01)
USPC ............. 436/180; 436/174; 436/179; 436/43; 422/64; 422/81; 422/547; 422/554; 422/501; 422/521

(58) Field of Classification Search
CPC ........ G01N 15/06; G01N 33/00; G01N 33/48
USPC ........ 422/64, 81, 547, 554, 501, 521; 436/43, 436/174, 179, 180
See application file for complete search history.

(56) References Cited

U.S. PATENT DOCUMENTS 4,106,671 A 8/1978 Sharples
(Continued)

FOREIGN PATENT DOCUMENTS

| | | |
|---|---|---|
| EP | 0035763 | 9/1981 |
| EP | 0754951 | 1/1997 |
| WO | 9117446 | 11/1991 |

OTHER PUBLICATIONS

Invitation to Pay Additional Fees and, Where Applicable, Protest Fee and Communication Relating to the Results of the Partial International Search, issued by the International Searching Authority in connection with corresponding International patent application No. PCT/US2010/038521 mailed on Nov. 9, 2010, 5 pages.
(Continued)

*Primary Examiner* — Brian J Sines
(74) *Attorney, Agent, or Firm* — Hanley, Flight & Zimmerman, LLC

(57) ABSTRACT

A system for managing bulk liquids for an automated clinical analyzer. The system comprises (a) at least one local reservoir for storing a bulk liquid for impending use, (b) at least one container for holding a bulk liquid before the liquid is transferred to a local reservoir, and (c) a controller for monitoring the level of a bulk liquid in a local reservoir. The local reservoir for storing a bulk liquid for impending use can be a trough. The use of troughs for storing a reagent, a diluent, or some other treating agent for impending use enables an aspirating/dispensing device having a plurality of pipettes to aspirate and dispense the reagent, diluent, or other treating agent at a high rate of throughput. The controller can monitor the level of a liquid in (a) a local reservoir for storing a bulk liquid for imminent use and the level of liquid in a (b) container for holding a bulk liquid before the liquid is transferred to a local reservoir. In the laboratory automation system described herein, the container for holding a bulk liquid before the liquid is transferred to a local reservoir can be a bottle. Other desirable features in the system include, but are not limited to, pump(s), valves, liquid level sensors.

15 Claims, 12 Drawing Sheets

(51) Int. Cl.

| | |
|---|---|
| ***G01N 33/48*** | (2006.01) |
| ***G01N 1/28*** | (2006.01) |
| ***G01N 35/10*** | (2006.01) |

(56) References Cited

U.S. PATENT DOCUMENTS

| | | | |
|---|---|---|---|
| 4,332,768 | A | 6/1982 | Berglund |
| 4,844,870 | A | 7/1989 | Rasmussen et al. |
| 4,933,147 | A | 6/1990 | Hollar et al. |
| 5,389,339 | A | 2/1995 | Petschek et al. |
| 5,641,006 | A | 6/1997 | Autrey et al. |
| 5,795,784 | A | 8/1998 | Arnquist et al. |
| 5,807,523 | A | 9/1998 | Watts et al. |
| 5,855,851 | A | 1/1999 | Matsubara et al. |
| 5,856,194 | A | 1/1999 | Arnquist et al. |
| 5,902,548 | A | 5/1999 | Watts et al. |
| 6,027,691 | A | 2/2000 | Watts et al. |
| 6,293,750 | B1 | 9/2001 | Cohen et al. |
| 7,033,543 | B1 | 4/2006 | Panzer et al. |
| 8,035,485 | B2 | 10/2011 | Fritchie |
| 2005/0056713 | A1 | 3/2005 | Tisone et al. |
| 2008/0024301 | A1 | 1/2008 | Fritchie et al. |
| 2009/0117620 | A1 | 5/2009 | Fritchie et al. |
| 2009/0181359 | A1 | 7/2009 | Lou et al. |
| 2010/0123551 | A1 | 5/2010 | Fritchie |

OTHER PUBLICATIONS

International Search Report, issued by the International Searching Authority in connection with corresponding International patent application No. PCT/US2010/038521, mailed on Aug. 19, 2011, 6 pages.

International Preliminary Report on Patentability and Written Opinion, issued by the International Searching Authority in connection with corresponding International patent application No. PCT/US2010/038521, mailed on Dec. 20 2011, 10 pages.

Architect Systems Operations manual (PN 201837-106), Jan. 2009, Sections 1-143 through 1-148, 6 pages.

"Level Switch Devices-Pressure Switch Instruments," Gems Sensors & Controls, Datasheet [Online], retrieved on Jun. 16, 2009 from [URL: http://www.gemsensors.com/] 2009, 2 pages.

ZEVEX, "LifeGuard Point Level Sensor," Datasheet [Online], Retrieved on Jun. 16, 2009 from [URL: http://www.zevex.com/sensing/pointlevel/], 2009, 2 pages.

Stewart, David, "Introduction to Real Time," retrieved on Jul. 29, 2014 from [URL:http://embedded.com/story/OEG20011016SO120], Nov. 1, 2001, 3 pages.

Office Action, issued by the United States Patent and Trademark Office in connection with U.S. Appl. No. 12/487,716, on Jan. 11, 2011, 8 pages.

Restriction and/or Election Requirement, issued by the United States Patent and Trademark Office in connection with U.S. Appl. No. 12/487,716, on Oct. 26, 2011, 5 pages.

Final Rejection, issued by the United States Patent and Trademark Office in connection with U.S. Appl. No. 12/487,716, on Jun. 21, 2012, 10 pages.

Restriction and/or Election Requirement, issued by the United States Patent and Trademark Office in connection with U.S. Appl. No. 12/487,716, on Feb. 4, 2013, 6 pages.

Office Action, issued by the United States Patent and Trademark Office in connection with U.S. Appl. No. 12/487,716, on Jun. 21, 2013, 9 pages.

Notice of Allowance and Fee(s) Due, issued by the United States Patent and Trademark Office in connection with U.S. Appl. No. 12/487,716, on Dec. 19, 2013, 8 pages.

SYSTEM FOR MANAGING INVENTORY OF BULK LIQUIDS

RELATED APPLICATION

This patent is a continuation of U.S. patent application Ser. No. 12/487,716, filed Jun. 19, 2009, entitled "System for Managing Inventory of Bulk Liquids," which is hereby incorporated herein in its entirety.

FIELD OF THE DISCLOSURE

This disclosure relates to managing the inventory of bulk liquids, and, more particularly, the managing of inventory of bulk liquids in an automated clinical analyzer.

BACKGROUND

Automated analyzers are well-known in the field of clinical chemistry and in the field of immunochemistry. Representative examples of such automated analyzers include, but are not limited to, PRISM® analyzers, AxSym® analyzers, ARCHITECT® analyzers, all of which are commercially available from Abbott Laboratories, Cobas® 6000, commercially available from Roche Diagnostics, Advia, commercially available from Siemens A G, Dimension Vista, commercially available from Dade Behring Inc., Unicel® DxC600i, commercially available from Beckman Coulter Inc., and VITROS, commercially available from Ortho-Clinical Diagnostics. Each of these analyzers suffers from various shortcomings, some more than others. Some of the shortcomings encountered by more than one of these automated analyzers include the use of large volumes of sample, the use of large volumes of reagents, the generation of large volumes of liquid waste and solid waste, and high costs. Some of the aforementioned automated analyzers are not designed so as to be able to carry out both clinical chemistry assays and immunoassays. Some of the aforementioned automated analyzers are not capable of being modified to suit the demands of certain users. For example, even if a user desires to have more immunoassay reagents on an analyzer and fewer clinical chemistry reagents on the analyzer, or vice versa, the user cannot modify the configuration. Furthermore, the addition of additional immunoassay modules and/or clinical chemistry modules to increase throughput is difficult, if not impossible. Some of the aforementioned automated analyzers require a great deal of maintenance, both scheduled and unscheduled. In addition, some of the aforementioned automated analyzers have scheduling protocols for assays that cannot be varied, i.e., the assay scheduling protocols are fixed, which limits such features as throughput. For example, modification of current assay protocols or addition of new assay protocols may be difficult, if not impossible. The ARCHITECT® analyzers currently in use can only support six variants of chemiluminescent microparticle immunoassay protocols. In addition, some of the aforementioned analyzers occupy a great deal of floor space and consume large quantities of energy.

Users of automated analyzers desire the automated analyzers to have a minimal effect on laboratory operations, i.e., occupancy of small areas of floor space, reduction of quantities of liquid waste and solid waste, reduction of quantities of reagents and samples used, capability of interacting with existing laboratory information management systems, and simplification of ordering of consumable items. Users of automated analyzers further desire more automation of processes, e.g., greater integration of immunoassays with clinical chemistry assays, automated loading of reagents, automated loading of other consumable items, automated removal of waste, and automated maintenance. Users of automated analyzers still further desire safer and more reliable apparatus, e.g., minimal quantity of unexpected failures, minimal down-time, minimal time required to diagnose and repair unexpected failures. Users of automated analyzers still further desire more trustworthy apparatus, e.g., consistent results across a plurality of interconnected analyzers, internal checks for verifying all assay processing steps, and self-diagnosing apparatus. Users of automated apparatus further desire quiet apparatus and environmentally friendly apparatus.

The management of bulk liquids used by automated clinical analyzers is typically performed manually. Consumers generally replenish bulk liquids on automated clinical analyzers based on need, i.e., a low inventory. The replenishment operation could reach a frequency that demands frequent, time-consuming monitoring by laboratory personnel. Accordingly, it is desired to automate the aforementioned operations in order to reduce the labor required to manage the inventory of bulk liquids in clinical analyzers.

SUMMARY

This disclosure provides a system for managing bulk liquids for an automated clinical analyzer. The system comprises (a) at least one local reservoir for storing a bulk liquid for impending use, (b) at least one container for holding a bulk liquid before the liquid is transferred to a local reservoir, and (c) a controller for monitoring the level of a bulk liquid in a local reservoir.

The local reservoir for storing a bulk liquid for impending use can be a trough. The use of troughs for storing a reagent, a diluent, or some other treating agent for impending use enables an aspirating/dispensing device having a plurality of pipettes to aspirate and dispense the reagent, diluent, or other treating agent at a high rate of throughput. The controller can monitor the level of a liquid in (a) a local reservoir for storing a bulk liquid for imminent use and the level of liquid in a (b) container for holding a bulk liquid before the liquid is transferred to a local reservoir. In the laboratory automation system described herein, the container for holding a bulk liquid before the liquid is transferred to a local reservoir can be a bottle. Other desirable features in the system include, but are not limited to, pump(s), valves, liquid level sensors.

The method described herein includes a method of reading information from labels. According to this method, radio frequency identification tags, conforming to the guidelines of ISO 14443 or ISO 15693 and ISO 18000, are positioned on the items of interest, such as, for example, containers for holding reagents (alternately referred to as "reagent containers"), containers for holding samples (alternately referred to as "sample containers"), and micro-well plates. These tags can be read by and written to by either a proving antenna of a radio frequency identification reader or a stationary antenna of a radio frequency identification reader. Reading of radio frequency identification tags and writing to radio frequency identification tags are controlled by software. The use of radio frequency identification technology provides faster and more reliable readings than barcodes, and further eliminates the hazards associated with laser scanning devices. The system described herein enables tracking of micro-well plates from the initial dispensing of samples and reagents to the final reading of results from the plates.

In another aspect, this disclosure provides a mechanism for loading local reservoirs. The local reservoir comprises a holder for holding a plurality of local reservoirs, e.g., troughs.

The holder is mounted upon a support. A first lever arm and a second lever one on each side of the support, are connected by a rod. The combination of the first lever arm, the second lever arm, and the rod allows a human operator to rotate a set of paddles. Each paddle supports one or more liquid level sensors that can be interfaced with receptacles for the sensors in the local reservoirs. In addition, tubes for filling and/or draining the local reservoirs are raised when the paddles are rotated to abut the local reservoirs and lowered when the paddles are rotated away from the local reservoirs.

The laboratory automation system described herein provides a user-friendly graphical user interface for enabling an operator closely control and monitor numerous immunoassays and/or clinical chemistry assays. The graphical user interface can utilize fuel gauge-type liquid level indicators to simplify reading of liquid levels in containers. The graphical user interface can utilize instructional balloons to instruct relatively inexperienced operators in proper usage of the laboratory automation system.

The system described herein reduces the labor required to manage the inventory of bulk liquids for automated clinical analyzers. Local reservoirs are monitored and replenished automatically. Other than initial loading of bulk liquids, intervention by an operator is not required.

Architectures of prior systems, such as, for example, ARCHITECT® clinical analyzers, that utilize direct liquid dispensing, with metering pumps, require more expensive pumps, valves, and the like, to carry out dispensing operations, and typically require priming after a container of bulk liquid is replaced or replenished. Because it is expected that air displacement pipetting will be used in the future to dispense bulk liquids, pumps for bulk liquids that replenish local reservoirs, including troughs, can be of lower cost, of lower volume (less than 1 liter/hour), and reduced metering. Finally valves are eliminated and only used for maintenance procedures. This allows clinical analyzers to be more reliable and cost less to repair.

Through the use of a liquid dispensing apparatus having a plurality of heads for holding pipette tips, bulk liquids can be transferred by inexpensive pumps, bulk liquids can be dispensed at low volumes, and metering is not required. The use of valves can be substantially eliminated, typically for use only for maintenance procedures, thereby enabling automated clinical analyzers to be more reliable and less costly to repair.

BRIEF DESCRIPTION OF THE DRAWINGS

In FIG. 8, the lever arms are shown rotated away from the troughs.

In FIG. 9, the lever arms are shown rotated away from the troughs.

FIG. 10 shows a peelable protective tape overlying receptacles for receiving liquid level sensors.

FIG. 11 shows the peelable protective tape overlying the receptacles for receiving liquid level sensors partially peeled away.

DETAILED DESCRIPTION

Figure 1:
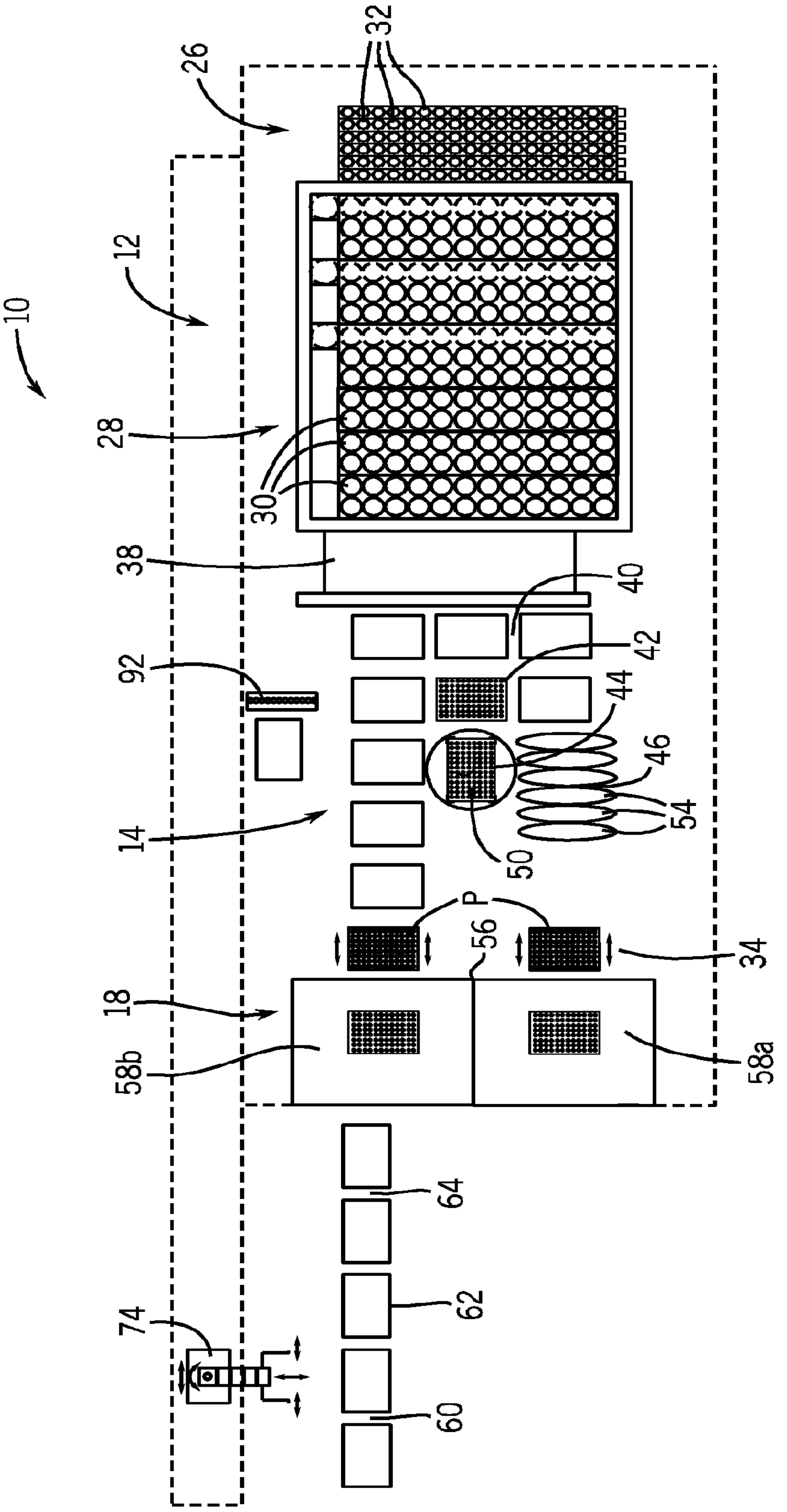
FIG. 1 is a top plan view of a laboratory automation system that employs bulk reagents in liquid form.

As used herein, the expression "bulk liquid" means a liquid, typically a reagent, a diluent, or some other type of treating agent in liquid form, which liquid is provided in a relatively large volume, e.g., one liter or greater. As used herein, the term "impending" means about to take place.

As used herein, the term "immunoassay" means a biochemical test that measures the concentration of a substance in a biological liquid, typically serum, using the reaction of an antibody or antibodies to its (their) antigen. An immunoassay takes advantage of the specific binding of an antibody to its antigen. As used herein, a "chemiluminescent microparticle immunoassay", alternatively referred to as "chemiluminescent magnetic immunoassay", involves a chemiluminescent label conjugated to the antibody or the antigen. In this assay, a magnetic microparticle is coated with antibodies. The assay is intended to look for antigens in the sample. A second antibody is labeled with a chemiluminescent label. This second antibody is not attached to a magnetic microparticle. The antibody and antigen with attach in the following order: antibody on magnetic microparticle-antigen-antibody-chemiluminescent label. The magnetic microparticle is then washed off. The amount of antibody-antigen-enzyme is measured by adding pre-trigger solution and trigger solution and measuring the light produced. This type of immunoassay produces light when combined with its substrate, i.e., a specific binding member. The chemiluminescent reaction offers high sensitivity and ease of measurement. This type of immunoassay involves a noncompetitive sandwich format that yields results that are directly proportional to the amount of analyte present in the sample. As used herein, the term "magnetic" means paramagnetic.

As used herein, the expression "clinical chemistry assay" means a biochemical test that measures the concentration of a substance that occurs naturally within the human body, which concentrations serves to indicate the condition or state of health of the various systems of the body. Such a substance, often referred to as an analyte, exists within certain expected ranges of concentration in a healthy human being. Chemistry analytes fall into one of three main categories, routine analytes, such as for example, lipids, nutrients, chemical constituents, metabolic products, examples of which include glucose, urea nitrogen triglycerides, uric acid, enzymes, such as, for example, alanine aminotransferase, aspartate aminotransferase, lactate dehydrogenase, and amylase, and electrolytes, such as, for example, sodium, potassium, and chloride. As used herein, the expression "laboratory automation system" means a system designed to automate the processing of samples prior to, during, and subsequent to analyzing the samples. The processing includes handling of the samples, moving the samples from a clinical analyzer to other components of the system, storing of the samples.

As used herein, the expression "radio frequency identification" is a generic term for technologies that use radio waves to automatically identify objects, such as, for example, containers for biological samples and containers for reagents for analyzing biological samples. The most common method of identification is to store a serial number that identifies the object, and perhaps other information relating to the object or contents thereof, on a microchip that is attached to an antenna. The microchip and the antenna together are called a radio frequency identification transponder or a radio frequency identification tag. The antenna enables the microchip to transmit the identification information and other information to a radio frequency identification reader. The radio frequency identification reader converts the radio waves reflected back from the radio frequency identification tag into digital information that can then be passed on to computers that can make use of it.

As used herein, the expression "radio frequency identification system", or "RFID system", comprises a radio frequency identification tag made up of a microchip with an antenna, and a radio frequency identification interrogator or radio frequency identification reader with an antenna. The radio frequency identification reader sends out electromagnetic waves. The tag antenna is tuned to receive these waves. A passive radio frequency identification tag draws power from the field created by the reader and uses it to power the circuits of the microchip. The microchip then modulates the waves that the passive radio frequency identification tag sends back to the radio frequency identification reader, which converts the waves received by the radio frequency identification reader into digital data.

As used herein, microchips in radio frequency identification tags can be "read-write microchips", "read-only microchips", or "write once, read many microchips." in the case of read-write microchips, information can be added to the radio frequency identification tag or existing information can be written over when the radio frequency identification tag is within range of a radio frequency identification reader. Read-write microchips usually have a serial number that cannot be written over. Additional blocks of data can be used to store additional information about the items to which the radio frequency identification tag is attached. These radio frequency identification tags can be locked to prevent overwriting of data or encrypted to prevent the disclosure of proprietary data or disclosure of data that would compromise the privacy of a patient. Read-only microchips have information stored on them during the manufacturing process. The information on them can never be changed. Write once, read many microchips have a serial number and other data written to them once, and that information cannot be overwritten later.

Active radio frequency identification tags have a transmitter and their own power source, typically a battery. The power source is used to run the microchip's circuitry and to broadcast a signal to a radio frequency identification reader. The microchip's circuitry can possibly perform some sort of monitoring function. Passive radio frequency identification tags have no battery. Instead, passive radio frequency identification tags draw power from the radio frequency identification reader, which sends out electromagnetic waves that induce a current in the tag's antenna. Semi-passive radio frequency identification tags use a battery to run the microchip's circuitry, but communicate by drawing power from the radio frequency identification reader. Any of the foregoing types of radio frequency identification tags can be used in the system of this disclosure.

As used herein, the expression "radio frequency identification reader" or "reader" means a device having the function of providing means for communicating with a radio frequency identification tag and facilitating transfer of data to and from a radio frequency identification tag. Functions performed by a radio frequency identification reader can include quite sophisticated signal conditioning, signal sorting, parity error checking, and correction. Once the signal from a radio frequency identification tag has been correctly received and decoded, algorithms can be applied to decide whether the signal is a repeat transmission, and can then instruct the radio frequency identification tag to cease transmitting. This type of interrogation is known as "command response protocol" and is used to circumvent the problem of reading a plurality of radio frequency identification tags in a short space of time. An alternative technique involves the radio frequency identification reader looking for radio frequency identification tags with specific identities, and interrogating them in turn. It is within the scope of this disclosure to use a single radio frequency identification reader or a plurality of radio frequency identification readers. A radio frequency identification reader is connected to a single antenna or to a plurality of antennas.

As used herein, the expression "aspirating/dispensing device" means a device that has the dual functions of removing liquids from containers by suction and distributing portions of the liquids aspirated into containers, e.g., micro-wells of micro-well plates. An aspiration/dispensing device that is capable of being used for the system described herein is described in U.S. Pat. No. 7,033,543, incorporated herein by reference. As used herein, the term "pipette", also called "pipet", "pipettor", means a laboratory instrument used to transport a measured volume of liquid. As used herein, the expression "micro-well plate", also called "microtiter plate", "microplate", means a flat plate having a plurality of "wells" used as small test tubes. As used herein, the term "XYZ" refers to a device that can move in three directions, a first horizontal direction, a second horizontal direction that is perpendicular to the first horizontal direction, and a third direction that is perpendicular to both the first horizontal direction and the second horizontal direction. As used herein, the expression "analysis section of the laboratory automation system" means that portion of the laboratory automation system in which immunoassays or clinical chemistry assays or both immunoassays and clinical chemistry assays are performed. As used herein, the term "kitting" means dispensing samples and reagents in appropriate micro-wells of a micro-well plate prior to commencing chemical reactions.

As used herein, the expression "local reservoir" means a container for holding a bulk liquid. Local reservoirs include closed containers and open containers. As used herein, the term "trough" means a local reservoir that is an open container.

As used herein, the term "channel" means a pipette tip. In general, the head of an aspirating/dispensing device has 12 channels or 96 channels.

As used herein, the term "system" means a group of interrelated, interacting, or interdependent constituents forming a complex whole. As used herein, the term "sub-system" means a subordinate system, i.e., a system that is a component of a larger system.

As used herein, the symbol "(s)" following the name of an item indicates that one or more of the subject items is intended, depending upon the context. As used herein, the expression "and/or" is used to indicate that either the word "and" or the word "or" can be used to connect words, phrases, or clauses.

Throughout the specification, so far as possible, like parts or components will have the same reference numerals; like parts or components may have different reference numerals when required for the sake of clarity. In addition, where necessary, a micro-well plate(s) is indicated by the letter "P". It should be noted the micro-well plates in processors and readers are not actually visible. However, the micro-well plates are inside of the processors and readers and the relative positions of the micro-well plates within the processors and readers are designated by the letter "P".

Laboratory automation systems employ automated clinical analyzers, such as, for example, automated immunoassay analyzers and automated clinical chemistry analyzers. Automated clinical analyzers typically employ aspirating/dispensing devices wherein a pipette (or pipettes) of the aspirating/dispensing device can be moved in three dimensions, i.e., two dimensions in a horizontal plane (i.e., X and Y) and one dimension vertically (i.e., Z). The remaining components of laboratory automation systems can be placed near to or be connected with the aspirating/dispensing device to enable the pipette for pipettes) to obtain access to various components of the laboratory automation system. However, not all components require direct access from an aspiration/dispensing device. In some cases, micro-well plates into which reagents have been dispensed can be moved out of the access range of the aspiration/dispensing device by an optional robotic mechanism and placed in an autonomous sub-system for further processing. In general, chemiluminescent microparticle immunoassays do not call for dispensing reagents after kitting has taken place. In contrast, clinical chemistry assays require dispensing reagents between readings.

Depending on the desired capabilities of the laboratory automation system, laboratory automation sub-systems (e.g., various diagnostic assay technologies) can added to or subtracted from the aspirating/dispensing device. In addition, multiple sub-systems can be added to the laboratory automation system to increase throughput, e.g., one or more immunoassay sub-systems can be added to an immunoassay subsystem to increase throughput of immunoassays, or one or more clinical chemistry assay sub-systems can be added to a clinical chemistry assay sub-system to increase throughput of clinical chemistry assays.

Figure 2:
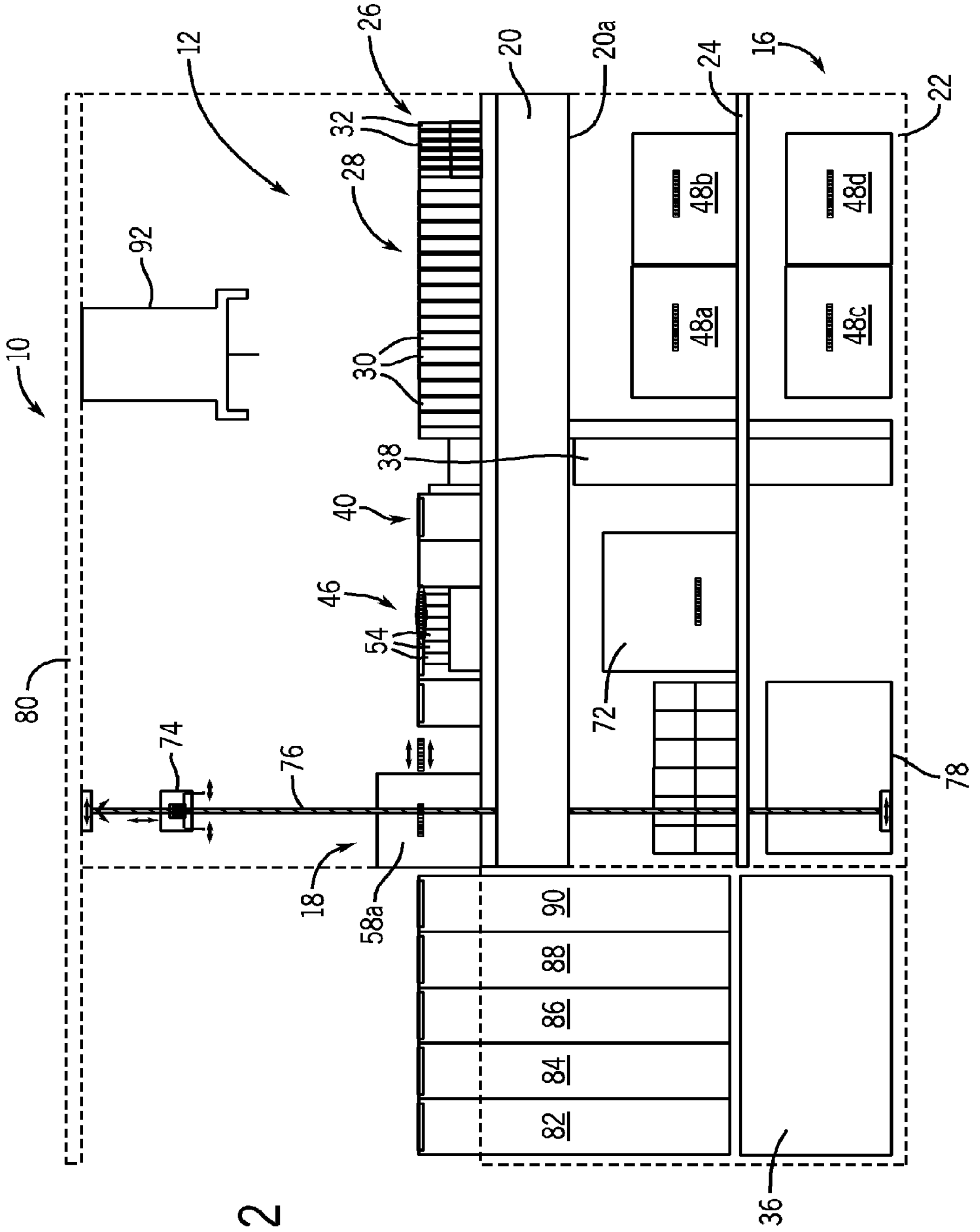
FIG. 2 is a side view in elevation of the laboratory automation system shown in FIG. 1.

The desired components of laboratory automation systems can be positioned in numerous arrangements. FIGS. 1 and 2 illustrate a sub-system of laboratory automation system. The sub-system shown in FIGS. 1 and 2 is an analysis section of a laboratory automation system, wherein immunoassays are integrated with clinical chemistry assays. This sub-system can also perform a relatively high number of assays per unit of time. A system for managing the inventory of reagents can be designed to place reagent containers into reagent container carriers, after which placement, these reagent container carriers will be routed to the analysis section of the laboratory automation system, where they will be diverted into the correct local queue. Reagent containers, reagent container carriers, and queues are described in detail in U.S. application Ser. No. 12/257,495, filed Oct. 24, 2008, and entitled AUTOMATED ANALYZER FOR CLINICAL LABORATORY, incorporated herein by reference.

A reagent inventory management system can be added to the laboratory automation system described herein. A typical reagent inventory management system includes an operator interface for the loading of boxes of reagents and other supplies, radio frequency identification system for identification of inventory and tracking, robotic mechanisms for loading containers onto the track system and removing containers from the track system, decapping equipment, refrigeration equipment, and information technology connections to laboratory analyzers and vendors.

Not shown in FIGS. 1 and 2, but necessarily present, is a control and ling information in the laboratory automation system. The control unit also provides the commands to the various robotic mechanisms, which carry out the automated functions of the laboratory automation system. It is expected that the control unit can be a personal computer.

A central reagent storage area (not shown) can provide a substantial inventory of reagents; these reagents can be transported to the track system (not shown) or the analysis section of the laboratory automation system as required. Means of transportation suitable for transporting reagents from the central storage area to an input/output module (not shown) include, but are not limited to, gantries, endless conveyor belts, and robotic mechanisms. The central reagent storage system, the track system, the input/output module are described in detail in U.S. application Ser. No. 12/257,495, filed Oct. 24, 2008, and entitled AUTOMATED ANALYZER FOR CLINICAL LABORATORY, previously incorporated herein by reference.

Adjacent to the track system is at least one analysis section 10 of the laboratory automation system. Depending upon the size of the track system, more than one analysis section 10 can be employed.

Referring again to FIGS. 1 and 2, the analysis section 10 has four major sub-sections, namely a sub-section 12 for retaining samples and reagents that are to be used in the assays, at least one sub-section 14 for retaining disposable components for the equipment needed to introduce and manipulate samples and reagents into reaction vessels, e.g., micro-well plates, at least one sub-section 16 for supporting instruments needed to carry out immunoassays, and at least one sub-section 18 for supporting instruments needed to carry out clinical chemistry assays. The sub-sections 16 and 18 are not required to be directly accessible to an aspiration/dispensing device and can utilize kitted micro-well plates. However, the sub-sections 16 and 18 generally have an aspiration/device that has direct access to micro-well plates. FIG. 2 shows that the analysis section 10 is divided among three levels. The uppermost level 20 supports samples in containers, reagents in containers, and disposable items, all of which need to be accessed by aspirating/dispensing devices. The lowermost level 22 supports liquid waste material and sub-systems that need to be accessed by a robotic gripping mechanism. The middle level 24 supports containers for bulk liquids that are loaded by an operator and sub-systems that need to be accessed by a robotic gripping mechanism.

An area 26 for holding sample containers, e.g., sample tubes, is positioned at one end of the analysis section 10. As shown in FIG. 1, the area 26 is capable of holding 108 sample tubes (6 rows, 18 sample tubes in each row). A fewer or greater number of sample tubes can be accommodated, if so desired. Adjacent to the area 26 is an area 28 for holding reagent containers. The area 28 is a refrigerated area. The reagent containers typically have radio frequency identification tags attached thereto. As shown in FIG. 1, the area 28 is capable of holding 180 reagent containers. For example, the area 28 is capable of holding 108 reagent containers for immunoassays and 72 reagent containers for clinical chemistry assays. A fewer or greater number of reagent containers can be accommodated, if so desired. A radio frequency identification reader (not shown) is positioned below the deck 20 *a* of the uppermost level 20. The purpose of the radio frequency identification reader is to read and to update radio frequency identification tags on reagent containers and sample tubes when an aspirating step is carried out or a scan inventory operation is carried out.

The uppermost level 20 of the analysis section 10 is preferably elevated to a level sufficient to accommodate a radio frequency identification reader (not shown) for reading information from radio frequency identification tags (not shown) attached to reagent containers. Radio frequency identification readers suitable for use herein are described in U.S. application Ser. No. 11/495,430, filed Jul. 28, 2006, and entitled SYSTEM FOR TRACKING VESSELS IN AUTOMATED LABORATORY ANALYZERS BY RADIO FREQUENCY IDENTIFICATION and in U.S. application Ser. No. 12/274,479, filed Nov. 20, 2008, and entitled SYSTEM FOR TRACKING VESSELS IN AUTOMATED LABORATORY ANALYZERS BY RADIO FREQUENCY IDENTIFICATION, both of which are incorporated herein by reference.

In order to implement the radio frequency identification system described herein, a radio frequency identification tag can be positioned on the lowermost portion of a container, e.g., a reagent container 30, or on a container carrier, e.g., a sample container carrier (not shown). It is often desirable to position an encapsulated radio frequency identification tag on the lowermost portion of a container. In the case of a sample container 32, a radio frequency identification tag can be positioned on the sample container carrier.

The radio frequency identification system includes at least one stationary radio frequency identification reader. In order for the at least one radio frequency identification reader to read the data from the radio frequency identification tag associated with a container, or with a container carrier, the container, or the container carrier, is caused to move to a position proximate to, and preferably in register with, the at least one radio frequency identification reader so that the information from the radio frequency identification tag can be read with an amount of noise and interference from nearby radio frequency identification tags on other containers, or on other container carriers, that are insufficient to adversely affect the integrity of the data read by a radio frequency identification reader. In this embodiment, a transmission sub-system need not be provided to enable the at least one radio frequency identification reader to move among the containers and the container carriers.

There are at least two ways to implement the foregoing embodiment of the stationary radio frequency identification reader. According to a first way, the sample containers and the reagent containers, or the sample container carriers and the reagent container carriers, can be transported to a position proximate to at least one stationary radio frequency identification reader, whereby the stationary radio frequency identification reader tags on the containers, or on the container carriers, can be read by the at least one stationary radio frequency identification reader. According to a second way, a plurality of antennas, which are traces on a printed circuit board, function as separate stationary radio frequency identification readers. These antennas can receive separate collections of data. In a preferred embodiment of a reader for reading radio frequency identification tags, a single printed circuit board has a plurality of antennas under the reagent storage area and the sample storage area. The length of the antenna is important, because the length determines the relationship with the radio frequency used. The length of the antenna corresponds to some multiple of wavelength of the radio frequency energy, e.g., one-half wavelength, one-quarter wavelength.

The printed circuit board for the radio frequency identification system can provide connections for remote antennas and a means for selecting those antennas one at a time. For example, the radio frequency identification system can have external connections for several remote reading locations, such as the micro-well plate rotator, pre-treatment area, magnetic particle processor, luminescence reader(s), absorbance reader(s), inventory reading locations, and locations on the local queue and transport track. By reading the antennas at these remote locations, a micro-well plate can be tracked throughout the laboratory automation system and provide a chain of custody.

Another radio frequency identification reader, which is stationary, reads radio frequency identification tags on micro-well plates. The use of radio frequency identification readers makes it possible to efficiently and tightly pack reagent containers 30 and sample containers 34 in the sub-section 12 of the analysis section 10 of the laboratory automation system. The use of radio frequency identification readers and radio frequency identification tags make it possible to include a higher density of data on a container, relative to the amount of data that can be applied by means of barcodes. Furthermore if writable radio frequency identification tags are used, the data on the radio frequency identification tags can be updated to reflect changes that have taken place with respect to the contents of the containers equipped with the radio frequency identification tags. The radio frequency identification system can provide an interface to personal computer.

A radio frequency identification reader can read and update radio frequency identification tags on reagent containers 30 and on sample containers 32, or on sample container carriers (not shown), when aspirating of a portion of the reagent or a portion of the sample is carried out or an operation for scanning the items in inventory is initiated. Information of the type shown in TABLE 1 can be updated on the radio frequency identification tags by the radio frequency identification reader.

TABLE 1

| Class of data | Specific data |
|---|---|
| Tag identifier | Unique identifier for container |
| Manufacturing data | (a) Revision number(s) of reagent(s)<br>(b) Serial number(s) of reagent(s)<br>(d) Component identifier(s)<br>(e) Lot number(s) of reagent(s)<br>(f) Stability/expiration data for reagent(s)<br>(g) Times/dates of manufacture of reagent(s)<br>(h) Configuration(s) of assay(s)<br>(e.g., number of reagent containers needed)<br>(i) Number of tests in container(s)<br>(j) Associated components of assay(s)<br>(k) Calibration data for assay(s) |
| Shipping and storage data | (a) Temperature(s) of reagent during shipping<br>(b) Times/dates of shipping movements and storage periods<br>(c) Locations and dates of storage periods |
| Analyzer and usage data | (a) Times/dates of opening(s) of reagent container(s)<br>(b) Number of aspirations from reagent container(s)<br>(c) Carryover and potential contamination or dilution of reagent(s) or sample(s)<br>(d) Encryption algorithms for protection of data<br>(e) Other algorithms to ensure integrity of data<br>(f) Chain of custody for operations performed on micro-well plates, reagent containers and sample containers; for micro-well plates, dispensing of samples, reagents(s), |

TABLE 1-continued

| Class of data | Specific data |
| --- | --- |
| | incubation temperature, processing, and readings; for reagent containers, date of manufacture, date of shipping, date of loading in reagent inventory management system, date of opening, date of loading into analyzer, aliquots removed and remaining, cumulative carryover, expiration date; for sample containers, draw date, patient, doctor, technicians, test orders, centrifugation, decapping, aliquots removed, cumulative carryover, resealing, entry into storage |

An area 34 located in front of the analysis section 10 of the laboratory automation system can be used as a radio frequency identification read zone for micro-well plates in order to track the micro-well plate for chain of custody purposes. By this means, analytical results can be traced to the micro-well plate in which a given assay was performed. A system for utilizing radio frequency identification tags and radio frequency identification readers is described in U.S. application Ser. No. 11/495,430, filed Jul. 28, 2006, and entitled SYSTEM FOR TRACKING VESSELS IN AUTOMATED LABORATORY ANALYZERS BY RADIO FREQUENCY IDENTIFICATION and in U.S. application Ser. No. 12/274,479, filed Nov. 20, 2008, and entitled SYSTEM FOR TRACKING VESSELS IN AUTOMATED LABORATORY ANALYZERS BY RADIO FREQUENCY IDENTIFICATION, both of which have been previously incorporated herein by reference.

A first area 36 for holding solid waste is positioned at the far left of the system. A second area 38 for holding solid waste is positioned adjacent to an upright brace of the structure supporting the upper level 20 and the middle deck 24 of the system. Solid waste includes pipette tips, micro-well plates, empty reagent containers, and tip combs used in immunoassay processors. An area 40 for holding reusable, disposable pipette tips is positioned on the upper level 20 adjacent to the second area 38 for holding solid waste. Disposable pipette tips can be reused for aspirating and dispensing the same reagent or for aspirating and dispensing the same sample. A pre-treatment and/or dilution area 42 is positioned adjacent the area 40 for holding reusable, disposable pipette tips. A small percentage of samples require pretreatment or dilution operations. Pre-treatment involves preparing a sample for testing of the sample by means of an immunoassay or a clinical chemistry assay or extracting from a sample an appropriate component for testing of the component by means of an immunoassay or a clinical chemistry assay. Dilution reduces the concentration of a component in a sample so that the component can be analyzed within dynamic range applicable to the immunoassay analyzer or clinical chemistry analyzer. Pre-treatment steps and dilution steps are carried out prior to immunoassay processing or clinical chemistry assay processing.

A kitting area 44 for kitting immunoassays is positioned between an area 46 that includes local reservoirs, i.e., the storage area for bulk liquids for impending use, and the area 40 for holding reusable, disposable pipette tips. Additions of sample, reagent, buffer, pre-trigger solution for up to twelve (12) immunoassays can be carried out in the kitting area 44 for kitting immunoassays. A micro-well plate, designated in general by the letter "P", to which samples, reagents, buffers, and pre-trigger solutions have been added can then be transferred to an immunoassay processor 48 *a*, 48 *b*, 48 *c*, or 48 *d*, for immunoassay processing. An immunoassay processor suitable for use herein is described in greater detail in U.S. application Ser. No. 11/923,828, filed Oct. 25, 2007, and entitled METHOD OF PERFORMING ULTRA-SENSITIVE IMMUNOASSAYS, and U.S. application Ser. No. 12/257,495, filed Oct. 24, 2008, and entitled AUTOMATED ANALYZER FOR CLINICAL LABORATORY, both of which are incorporated herein by reference. Clinical chemistry samples can be dispensed in the kitting area 44 for kitting immunoassays when that area 44 is not being used for kitting immunoassays. Additions of samples for four (4) to sixteen (16) patients can be dispensed in the kitting area 44. A plate rotator 50 can rotate the micro-well plate 90° for addition of clinical chemistry reagents. The storage area 46 for bulk liquids for impending use is positioned adjacent the plate rotator 50. In the storage area 46 for bulk liquids for impending use, troughs 54 can be used to store liquid reagents in bulk for immunoassays and liquid reagents in bulk for clinical chemistry assays prior to impending use. Radio frequency identification readers can be used to read and update radio frequency identification tags attached to micro-well plates to record the chain of custody of the micro-well plates. A clinical chemistry assay processing area 56 is positioned on the upper level 20 and on the middle level 24. Absorbance readers 58 *a*, 58 *b* can be used to interleave reading with additions of various reagents. A loading area 60 for micro-well plates as positioned at the far left of the analysis section 10 and above the first area 36 for holding solid waste. Micro-well plates are stored in the area 60 prior to use. A loading area 62 for tip combs is positioned adjacent to the loading area 60 for micro-well plates and above the first area 36 for holding solid waste. Tip combs are stored in this area prior to use. Tip combs are disposable items used with certain types of immunoassay processors, more specifically, immunoassay processors employing separation of reaction components by means of magnetic particles. A loading area. 64 for disposable pipette tips is positioned adjacent to the loading area 62 for tip combs and above the first area 36 for holding solid waste. Racks for disposable pipette tips can be used to store disposable pipette tips prior to use. Further description of the various items located in the aforementioned areas can be found in U.S. application Ser. No. 12/257,495, filed Oct. 24, 2008, and entitled AUTOMATED ANALYZER FOR CLINICAL LABORATORY, previously incorporated herein by reference.

As mentioned previously with respect to FIG. 2, it can be seen the analysis section 10 is divided into three levels 20, 22, and 24, whereby the quantity of floor area required for the components of the analysis section 10 of the laboratory automation system can be reduced. In addition, the multiple-level configuration makes it easier to have some immunoassay analyzers dedicated to routine testing and some immunoassay analyzers dedicated to STAT testing. The sample containers 32, e.g., sample tubes, and the reagent containers 30 are positioned on the uppermost level 20. Absorbance readers 58 *a*, 58 *b* for clinical chemistry assays are positioned on the upper level 20 and the middle level 24, and immunoassay processors 48 *a*, 48 *b*, 48 *c*, and 48 *d* for immunoassay processing are positioned on the piddle level 24 and the lowermost level 22.

A luminescence reader(s) 72 for immunoassays is (are) positioned separate from the immunoassay processors 48 *a*, 48 *b*, 48 *c*, 48 *d* at the sub-section 16 of the analysis section 60. The luminescence reader(s) 72 read the results of the immunoassay from micro-well plates after the reaction mixtures have been processed in the immunoassay processors 48*a*, 48 *b*, 48 *c*, 48 *d*. The micro-well plates can be transferred from the immunoassay processor(s) 48 *a*, 48 *b*, 48 *c*, 48 *d* to the luminescence reader(s) 72 by means of a conveyor belt (not shown). Alternatively, the micro-well plates can be transferred from the immunoassay processor(s) 48 *a*, 48 *b*, 48 *c*, 48 *d* to the luminescence reader(s) 72, by means of a robotic mechanism. Luminescence readers suitable for use herein are commercially available under such trade names as Molecular Devices LMax II 384 and Thermo Scientific Luminoskan® Ascent. The items shown in FIG. 2 are described in greater detail in U.S. patent application Ser. No. 12/257,495, filed Oct. 24, 2008, and entitled AUTOMATED ANALYZER FOR CLINICAL LABORATORY, incorporated herein by reference.

A robotic gripping device 74 is capable of moving vertically by means of a threaded screw 76. Attached to the robotic gripping device 74 is a nut (not shown) that enables the robotic gripping device 74 to move vertically along the threaded screw 76. Movement of the nut can be actuated by a motor (not shown), typically a stepper motor. The robotic gripping device 74 is further capable of moving in a horizontal direction along tracks 78 and 80, which are dedicated to the robotic gripping device 74. The robotic gripping device 74 can be designed to have features to enable telescoping movement and rotational movement. The telescoping feature enables the robotic gripping device 74 to be extended or retracted in order to reach positions located between the front of a clinical analyzer and the rear of a clinical analyzer. The rotational feature facilitates the gripping, raising, lowering, and placing of micro-well plates in positions desired. It should be noted that the analysis section 10 can employ more than three levels or fewer than three levels. Also shown in FIGS. 1 and 2 are stacker drawers 82, 84, 86, 88, and 90 for storing and dispensing disposable items, such as, for example, micro-well plates, tip combs for immunoassay processors, and disposable pipette tips. The use of stacker drawers 82, 84, 86, 88, and 90 enables the system to draw supplies from stacks loaded by an operator. Such stacks result in reduction of floor space requirements. Stacker drawers 82, 84, 86, 88, and 90 make it possible to store consumable items vertically. The analysis section 10 also has an aspirating/dispensing device 92 for aspirating and dispensing reagents, samples, and bulk liquids. The aspirating/dispensing device 92 is an XYZ device that is capable of moving in three directions. The aspirating/dispensing device 92 need not have the capability of functioning as a gripping device for reagent containers or micro-well plates or both containers and micro-well plates. However, this capability can enhance the automated features of a laboratory automation system. On the lowermost level 22, positioned adjacent to the area 36 for holding solid waste, is an area 94 for holding liquid waste. Liquid waste includes waste from maintenance procedures.

Sample containers, reagent containers, radio frequency identification readers, kitting immunoassays, kitting clinical chemistry assays, immunoassay processors, micro-well plates, tip combs, disposable tips are described in greater detail in U.S. application Ser. No. 12/257,495, filed Oct. 24, 2008, and entitled AUTOMATED ANALYZER FOR CLINICAL LABORATORY, previously incorporated herein by reference. U.S. application Ser. No. 12/257,495 also describes a track system suitable for a laboratory automation system. Also described in greater detail in U.S. application Ser. No. 12/257,495, filed Oct. 24, 2008, are clinical chemistry analyzers and immunoassay analyzers. Still further described in greater detail in U.S. application Ser. No. 12/257,495, filed Oct. 24, 2008, are aspirating/dispensing devices and robotic gripping devices.

Bulk liquids are contained in local reservoirs, such as, for example, troughs, so that they will be available for dispensing by a robotic dispensing device. Proper levels of liquid in local reservoirs or troughs can be maintained by an operator. However, access to replenish bulk liquids would not be continuous. Accordingly, replenishment of bulk liquids would be scheduled, because a moving dispensing device would subject the operator to injury. In addition, the frequency of replenishment activities would be inconvenient for operators.

Figure 3:
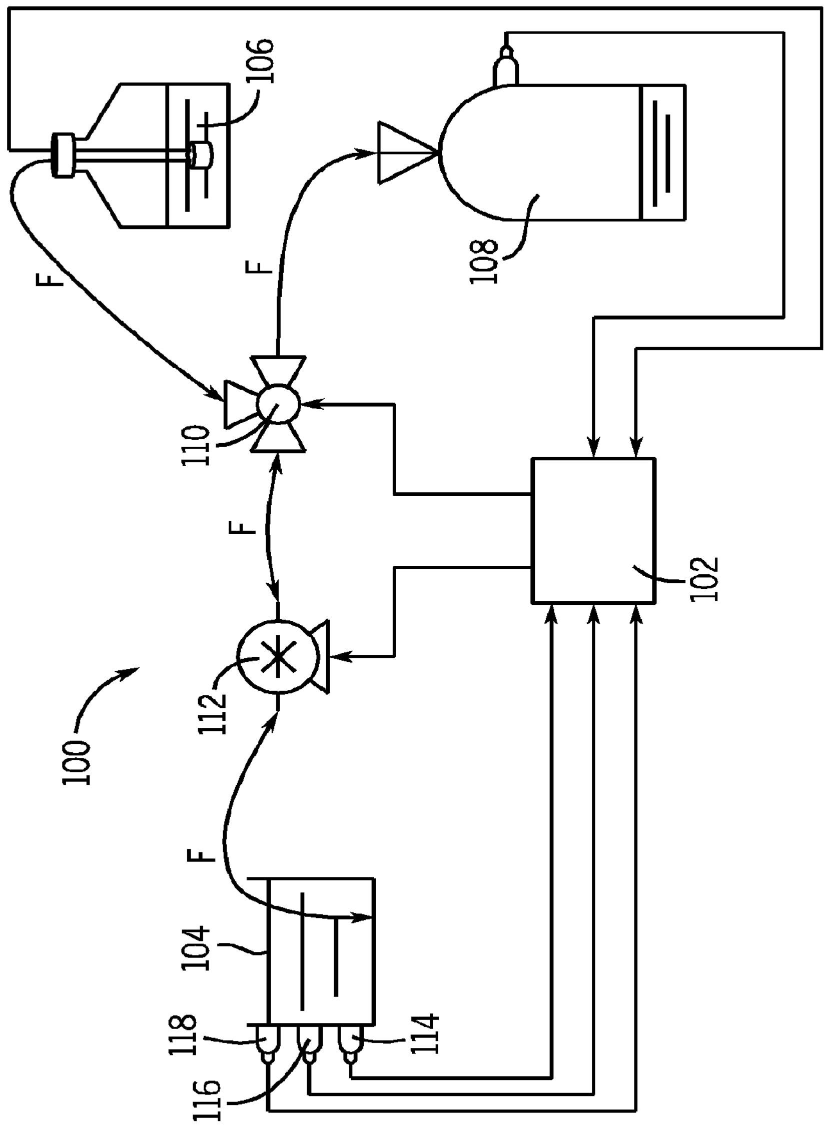
FIG. 3 is a schematic diagram of the bulk liquid handling system described herein.

Referring now to FIG. 3, a sub-system 100 for replenishing bulk liquids comprises a bulk liquid handling controller 102, which interfaces with a plurality of channels, each channel dedicated to a different bulk liquid. Referring now to FIG. 3, the controller 102 for handling bulk liquids comprises a central processing unit, memory, interfaces to liquid level sensors, motor controllers, other hardware components, and an interface to a real-time controller. A trough 104 for a bulk liquid is typically formed from a polymeric material that is resistant to corrosion. The dimensions of a trough 104 having a volume of approximately 100 milliliters can be approximately 1 inch wide×4.5 inches long×2 inches deep. A container 106 for a bulk liquid is typically formed of a polymeric material that is resistant to corrosion. The dimensions of a container 106 for bulk liquid having a volume of approximately 1 liter can be approximately 7 inches deep×2.5 inches wide×4.5 inches long. A waste container 108 or drain (not shown) is typically formed of a polymeric material that is resistant to corrosion. The dimensions of a waste container or a drain having a volume of approximately 10 liters can be approximately 15 inches wide×7 inches high×9 inches deep. An electronic switching valve 110 for selecting the waste container or the drain can be a two-way valve and is normally connected to the container for bulk liquids. Upon a maintenance procedure, the valve is switched to the waste container or drain, and the pump is reversed, thereby pumping liquid from the local reservoir, or trough, into the waste container or the drain. Instead of a switching valve 110, a first check valve (not shown) can be used to only allow liquid to be drawn from a container for bulk liquids, and a second check valve (not shown) can be used to only allow liquid to enter the liquid waste facility, either a container or a drain. Thus, an active valve can be eliminated when the direction of the pump is reversed. A pump 112 for transferring small, unmetered volumes of liquids is typically a reversible, brushless DC motor-driven peristaltic pump with replaceable tubing.

Liquid level sensing requirements for local reservoirs and troughs present several compatibility issues. Compatibility issues arise from the interactions between the materials constituting the bulk liquids and the materials from which liquid level sensors are constructed. On account of compatibility issues, a non-intrusive liquid level sensor is preferred. A non-intrusive sensor is a sensor in which the level of liquid can be determined without having the sensor contact the liquid. N on-intrusive sensors suitable for use herein are commercially available from Gems Sensors & Controls, Plainville, Conn. and Zevex, Inc., Salt Lake City, Utah. Non-intrusive liquid sensors commercially available from Gems Sensors & Controls are sold under the trademark "ExOsense". Additional information relating to non-intrusive liquid level sensors can be found at the world wide web at http://www.gemssensors.com/ and http://www.zevex.com/sensing/pointlevel/, both of which are incorporated herein by reference. Capacitative sensors are not sufficiently stable when used in the absolute mode. Piezo-resonant sensors are capable of sensing the level of liquid through the wall of a container or trough. The liquid level sensor can be attached to a wall of a container or trough by means of an adhesive, such that the liquid level sensor is compressed against an interface material, which is positioned between the liquid level sensor and the wall of the container or trough. The interface material provides a signal path for the liquid level sensor. Each reservoir and trough preferably has three liquid level sensors: a low level sensor, a full level sensor, and an overfull level sensor. The system for handling bulk liquids will maintain the level of liquid between the low level sensor and the full level sensor. If an overfull level sensor is triggered, the system for handling bulk liquids will be shut off to prevent an overflow condition, which constitutes a safety hazard. As shown in FIG. 3, liquid level sensors 114, 116, and 118 can be attached to the local reservoir, e.g., a trough. A low level sensor 114 indicates when the liquid resides at 20% of the capacity of the local reservoir; a full level sensor 116 indicates when the liquid resides at 80% of the capacity of the local reservoir; and an overfill sensor 118 indicates when the liquid resides at 100% of the capacity of the local reservoir. In FIG. 3, the arrows designated by the letter "F" indicate the direction of flow of the bulk liquid. When arrow has two heads, the bulk liquid can flow in two directions.

The controller 102 for the bulk liquid handling system, hereinafter alternatively referred to as a bulk liquid handling controller, maintains the level of liquid in a local reservoir 104, e.g., a trough, on the deck supporting the aspirating/dispensing device. The bulk liquid handling controller 102 prevents overflow conditions from occurring at the local reservoirs 104, particularly troughs. The bulk liquid handling controller 102 allows access to the local reservoirs 104 by the aspirating/dispensing device. The bulk liquid handling controller 102 maintains the level of liquid without interaction from a real time controller.

The bulk liquid handling controller 102 tracks the volume of liquid remaining in the containers of bulk liquids. The bulk liquid handling controller 102 allows for continuous access to replace containers of bulk liquids. The bulk liquid handling controller 102 eliminates the need to prime channels after replacing containers of bulk liquids, such as, for example, bottles of bulk liquids. The bulk liquid handling controller 102 allows for the disposal of troughs at specified intervals. The bulk liquid handling controller 102 handles removal of liquid waste. The bulk liquid handling controller 102 provides access to optional liquid-handling accessories, such as, for example, an ARCHITECT® Automatic Reconstitution Module. The ARCHITECT® Automatic Reconstitution Module is an accessory that automatically dilutes concentrated wash buffer to the proper concentration and delivers it to a wash buffer reservoir. The ARCHITECT® Automatic Reconstitution Module is described in greater detail in ARCHITECT System Operations Manual (PN 201837-106) January 2009, pages 1-143 through 1-148, incorporated herein by reference. The bulk liquid handling controller 102 provides the capability to clean local reservoirs, e.g., troughs. A plurality of channels can be used for various different types of bulk liquids, such as wash buffer, water, pre-trigger solution, and the like. Each channel is capable of operating independently (a first channel can be maintaining the level of liquid in a trough while a second channel can be employing a cleaning solution in the cleaning step of a maintenance procedure).

Figure 4:
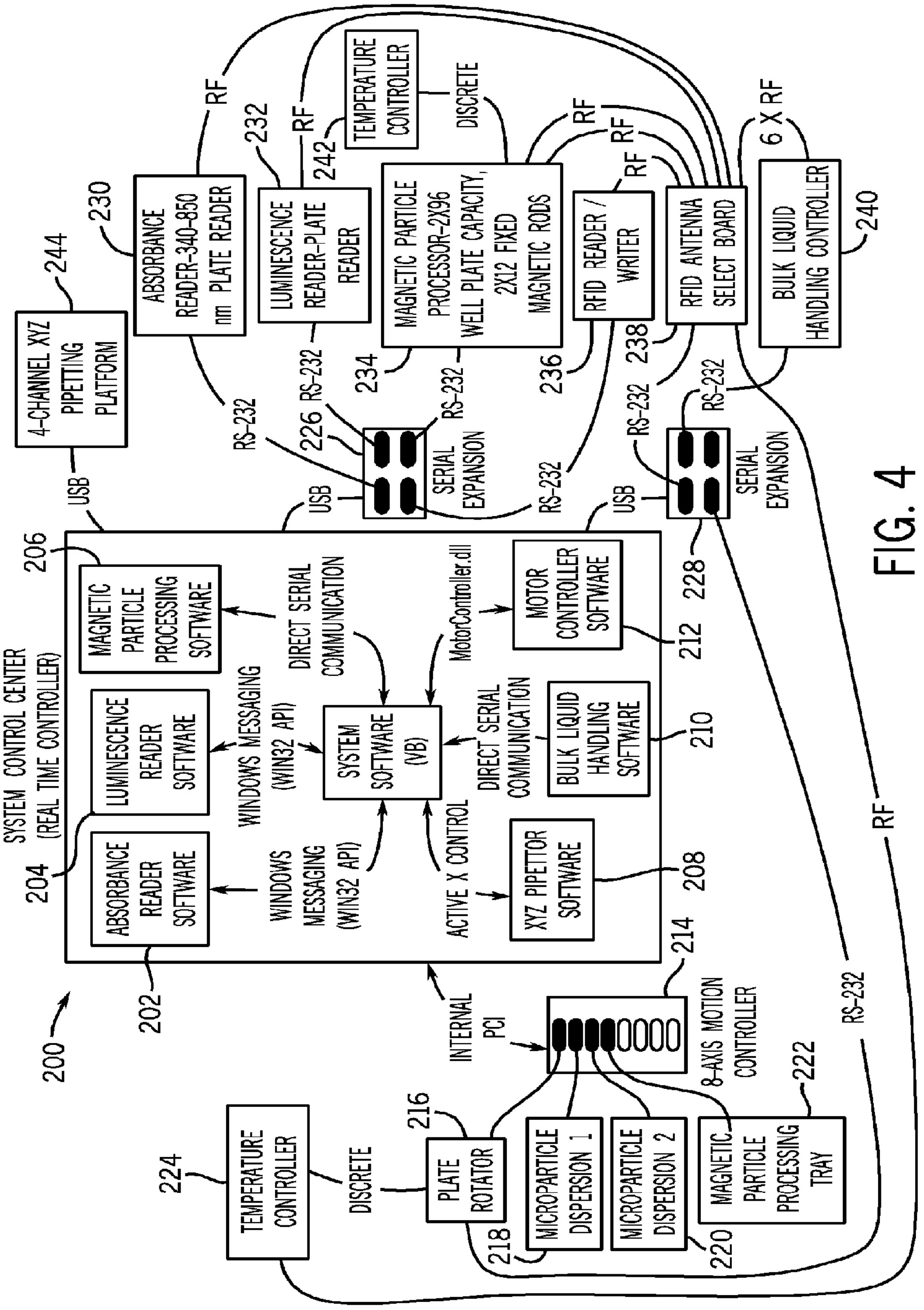
FIG. 4 is a schematic diagram illustrating the system control center for the laboratory automation system.
Figure 5:
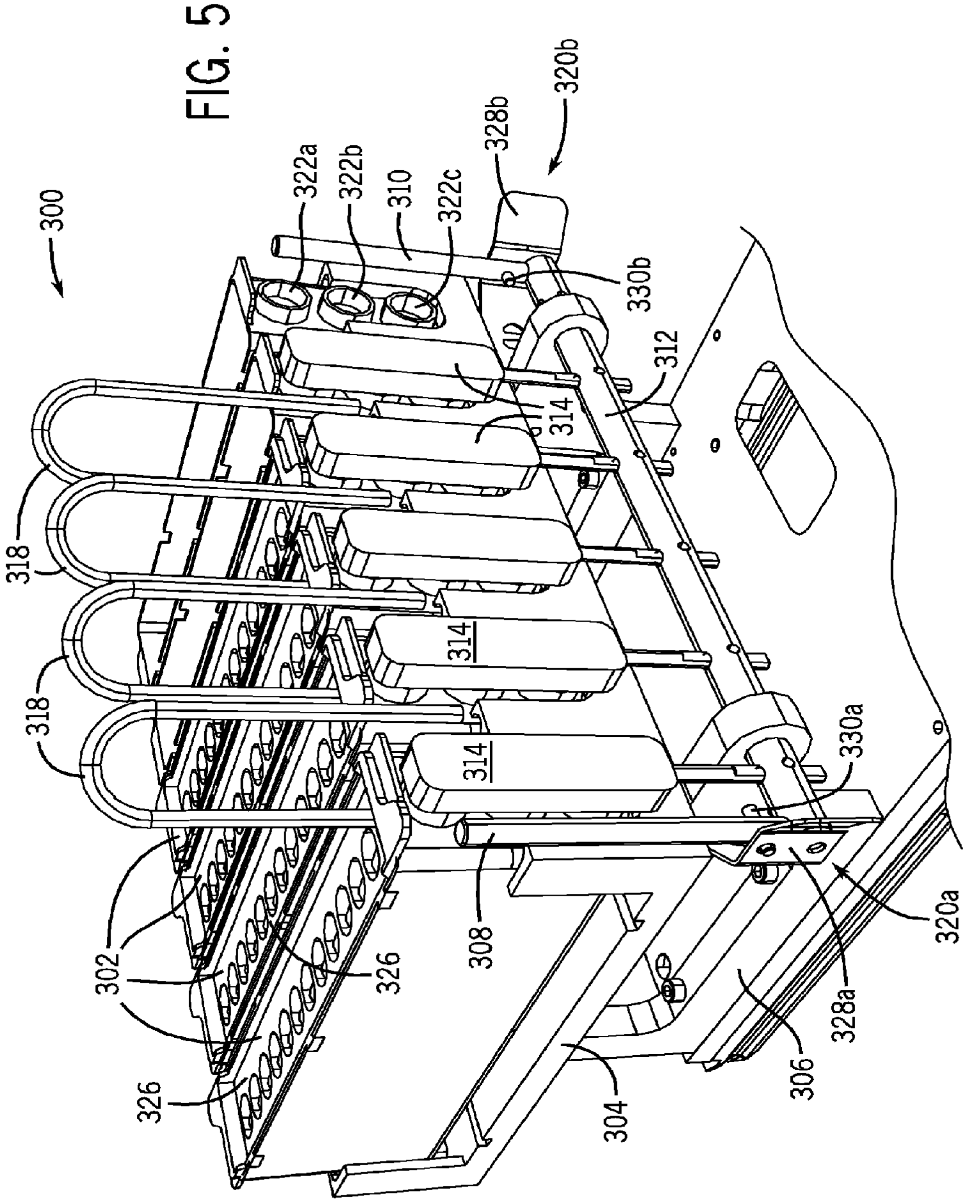
FIG. 5 is a perspective view of a mechanism for loading troughs that contain bulk reagents in liquid form.
Figure 6:
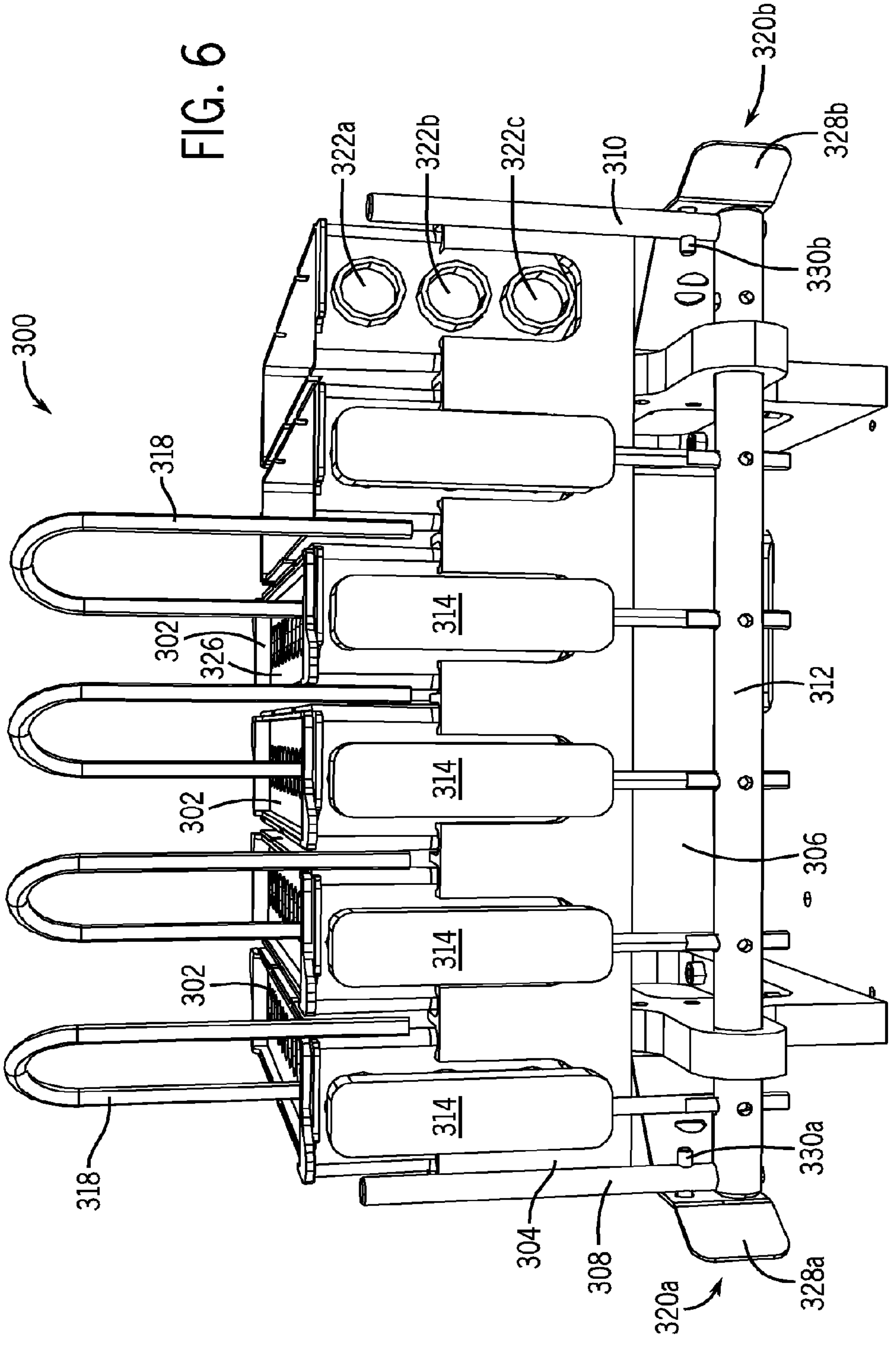
FIG. 6 is another perspective view of the mechanism shown in FIG. 5.
Figure 7:
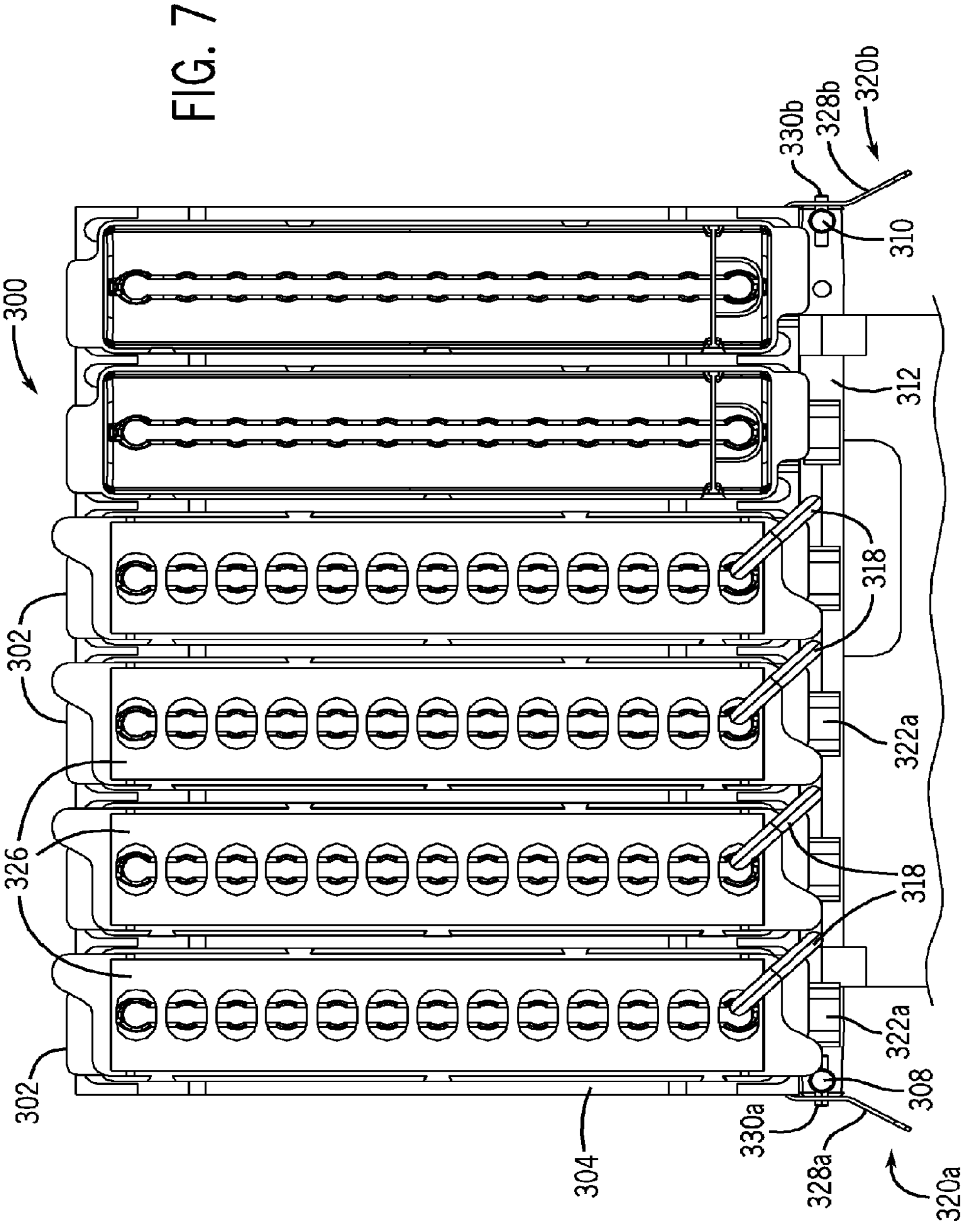
FIG. 7 is a top plan view of the mechanism shown in FIGS. 5 and 6.
Figure 8:
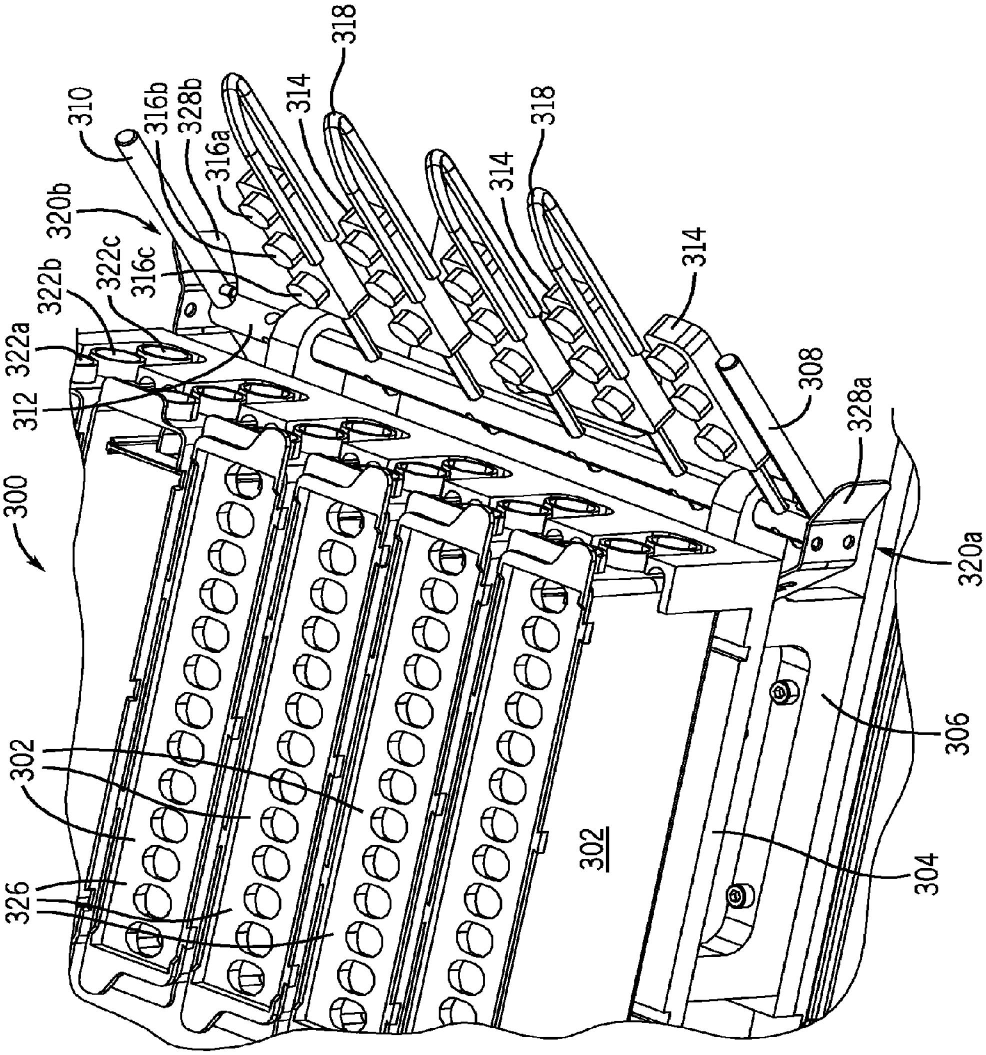
FIG. 8 is a partial perspective view of the mechanism shown in FIG. 5.
Figure 9:
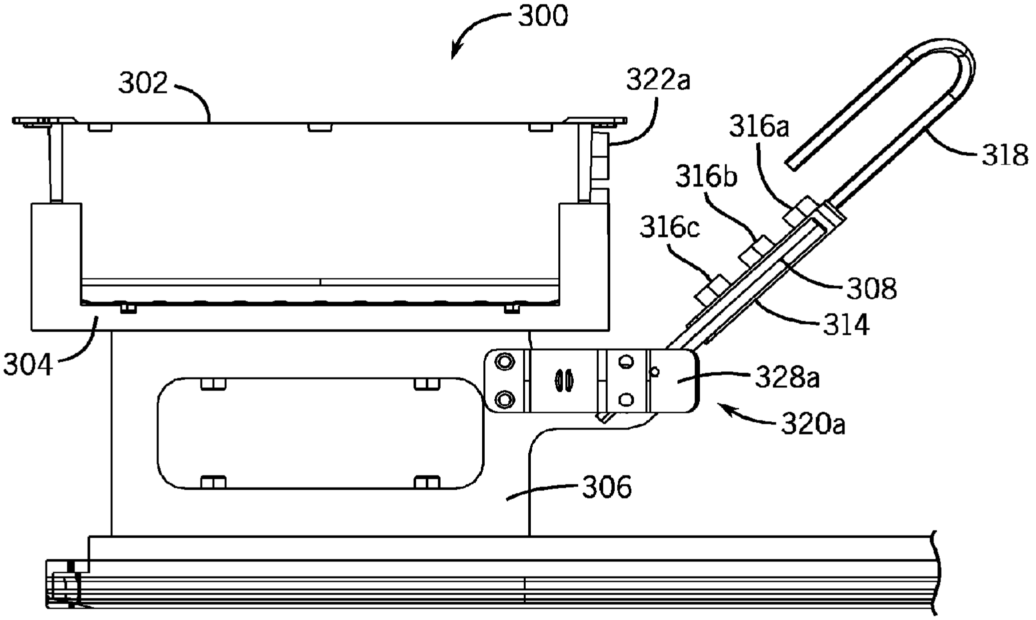
FIG. 9 is a side view in elevation of the mechanism shown in FIG. 8.

Control by means of the bulk liquid handling controller 102 allows the bulk liquid handling sub-system 100 to be activated or deactivated by a real time controller of a hi level system. The real time controller can request the status of the bulk liquid handling sub-system 100 or initiate a cleaning procedure. This control architecture would free the real time controller from the details of the operations of bulk liquid handling. FIG. 4 shows the relationship between the system for handling hulk liquids and the real time controller of a laboratory automation system. Real time control between a laboratory automation system and a bulk liquid handling sub-system allows a laboratory automation system and the bulk liquid handling system to coordinate their functions. For example, when a liquid in a container of bulk liquid is to be transferred to a local reservoir, a message is sent to the bulk liquid handling system. Then the bulk liquid handling system sends a message to the laboratory automation system to move the liquid from the container of bulk liquid to the appropriate local reservoir. Real time control is further described in Stewart, Introduction to Real Time, Embedded Systems Design—Embedded.com, Nov. 1, 2001, at the world wide web at http://www.embedded.com/story/OEG20011016S0120, incorporated herein by reference.

As shown in FIG. 4, a system control center, i.e., real time controller, 200 includes software for an absorbance reader 202, software for a luminescence reader 204, software for magnetic particle processing 206, software for an aspirating/dispensing device 208, software for a bulk liquid handling sub-system 210, and software for motor controller 212. The aforementioned software is connected to system software by means of appropriate interfaces. The system control center 200 is connected to an 8-axis motion controller 214 by means of an appropriate interface. The eight-axis motion controller 214 is connected to a plate rotator 216, a first microparticle reagent dispersing apparatus 218, a second microparticle dispersing apparatus 220, and a magnetic particle processing tray 222 by means of appropriate interfaces. The plate rotator 216, i.e., the location where dispensing is carried out, is connected to a temperature controller 224 by an appropriate interface. Also shown in FIG. 4 are a first serial expansion component 226 and a second serial expansion component 228. The first serial expansion component 226 is connected to at least one absorbance reader 230, to at least one luminescence reader 232, to at least one magnetic particle processor 234, and to at least one radio frequency identification reader/writer 236. The connections between the first serial expansion component 226 and the components attached thereto are made by appropriate interfaces, such as, for example, RS-232 connectors. The second serial expansion component 228 is connected to at least one radio frequency identification antenna select board 238, to at least one of the temperature controllers 224, and to a bulk liquid handling controller 240. The connections between the second serial expansion component 228 and the components attached thereto are made by appropriate interfaces, such as, for example, RS-232 connectors. Another component shown in FIG. 4 is a temperature controller 242, which is connected to the at least one magnetic particle processor 234 by an appropriate interface. Still another component connected to the system control center 200 is a four-channel XYZ aspirating/dispensing apparatus 244. The first serial expansion component 226, the second serial expansion component 228, and the four-channel XYZ aspirating/dispensing apparatus 244 are connected to the system control center 200 by means of appropriate interfaces, such as, for example, USB connectors.

Referring now to FIGS. 5, 6, 7, 9, 10, 11, and 12, a mechanism 300 for loading troughs 302 comprises a holder 304 for supporting a plurality of troughs 302. The holder 304 is mounted upon a support 306. A first lever arm 308 and a second lever arm 310, one on each side of the support 306, are connected by a rod 312. The combination of the first lever arm 308, the second lever arm 310, and the rod 312 allows the operator to rotate a set of paddles 314. Although two lever arms are shown in FIGS. 5, 6, 7, and 8, the rotation called for can be carried out by means of a single lever arm. Each paddle 314 supports three sensors 316 *a*, 316 *b*, 316 *c* for each trough 302. In addition, tubes 318 for filling and/or draining the troughs 302 are raised when the paddles 312 are rotated to abut the troughs 302 and lowered when the paddles 314 are rotated away from the troughs 302. Locking mechanisms 320 *a*, 320 *b* for the first lever arm 308 and the second lever arm 310, respectively, can be used to lock the first lever arm 308 and the second lever arm 310, respectively, to retain the paddles 314 in a specified position. The locking mechanisms 320 *a*, 320 *b* can easily be disengaged from the first lever arm 308 and from the second lever arm 310, respectively, to enable the paddles 314 to be rotated away from the troughs 302. Each trough 302 has three receptacles 322 *a*, 322 *b*, 322 *c* for containing an interface material (not shown) for the sensors 316 *a*, 316 *b*, and 316 *c*. This interface material is protested by a peelable protective strip 326, which can be removed prior to loading the trough 302 into the trough loading mechanism 300. The design of the trough 302 can optionally provide for a slip-in divider wall 326, which aids in guiding the tubes 318 in filling and/or draining the troughs 302.

The components of the trough loading mechanism 300 and the troughs 302 themselves are typically made of a durable, corrosion resistant material, such as, for example a polymeric material or a corrosion resistant metal or alloy. The trough loading mechanism 300 can be operated manually by a human operator or can be operated automatically by a robotic mechanism. The locking mechanisms 320 *a*, 320 *b* shown in FIGS. 5, 6, 7, 8, and 9 are more suitable for human operators in that each of these locking mechanisms 320 *a*, 320 *b* employ locking plates 328 *a*, 328 *b*, respectively, having an aperture therein. When the apertures of the locking plates 328 *a*, 328 *b* are in register with apertures formed in the first lever arm 308 and the second lever arm 310, respectively, the human operator can insert bolts 330 *a*, 330 *b* through the apertures in the locking plates 328 *a*, 328 *b* and through the apertures in the first lever arm 308 and the second lever arm 310, thereby locking the first lever arm 308 and the second lever arm 310 in a specified position.

Figure 10:
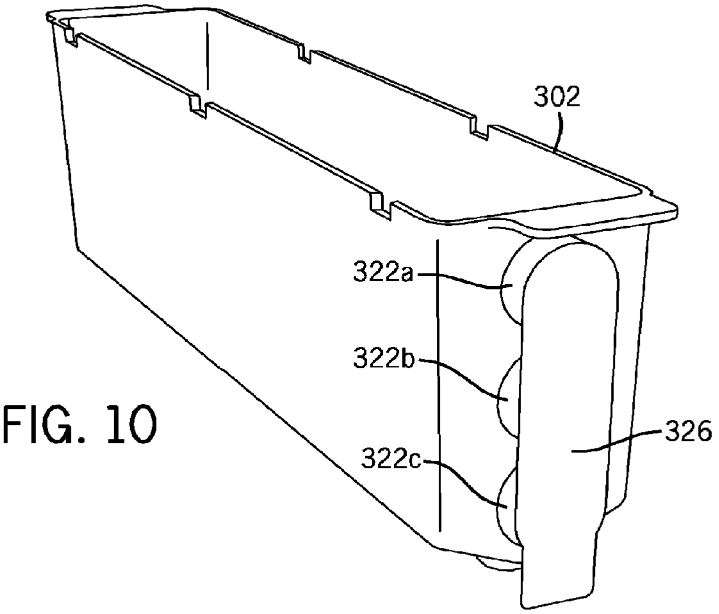
FIG. 10 is a perspective view of a trough suitable for holding hulk liquids.
Figure 11:
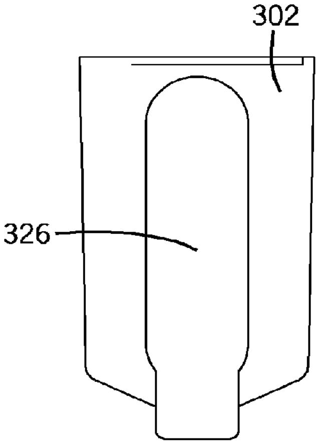
FIG. 11 is a side view in elevation of one end of the trough of FIG. 10.
Figure 12:
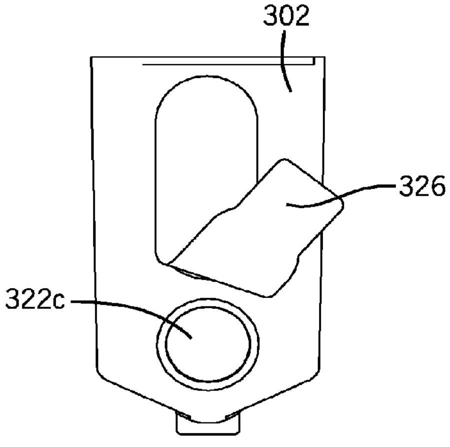
FIG. 12 is a side view in elevation of one end of the trough of FIG. 10.

As shown in FIGS. 5, 6, 7, 8, 9, and especially in FIGS. 10, 11, and 12, each trough 302 has a base 302 *a*, two elongated sidewalls 302 *b*, 302 *c* arising from the base 302 *a*, and two end walls 302 *d*, 302 *e* arising from the base 302 *a*. As an alternative to using the tube 318 to drain the trough, the trough 302 can be drained by opening an aperture (not shown) in the base 302 *a* of the trough 302.

Figure 13:
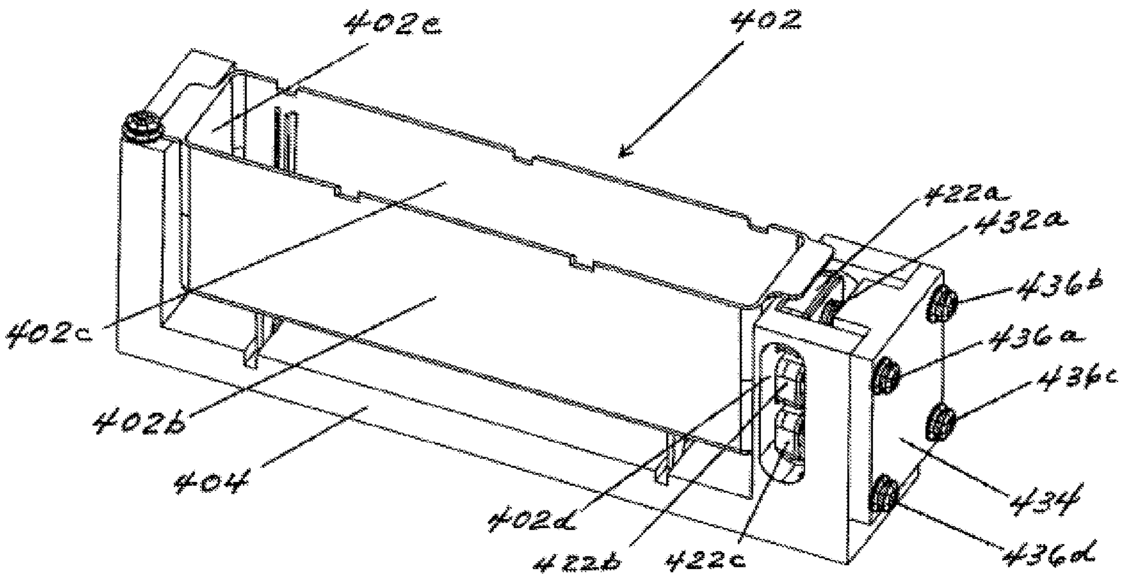
FIG. 13 is a perspective view of an alternative embodiment for attaching liquid level sensors to a trough.

In an alternative embodiment, the trough loading mechanism 300 is not required. In this alternative embodiment, shown in FIG. 13, a trough 402 is supported by a holder 404. The holder 404 is mounted on a support (not shown). The trough 402 has a base 402 *a*, two elongated sidewalls 402 *b*, 402 *c* arising from the base 402 *a*, and two end walls 402 *a*, 402 *e* arising from the base 402 *a*. The trough 402 can be drained by opening an aperture (not shown the base 402 *a* of the trough 402.

Figure 14:
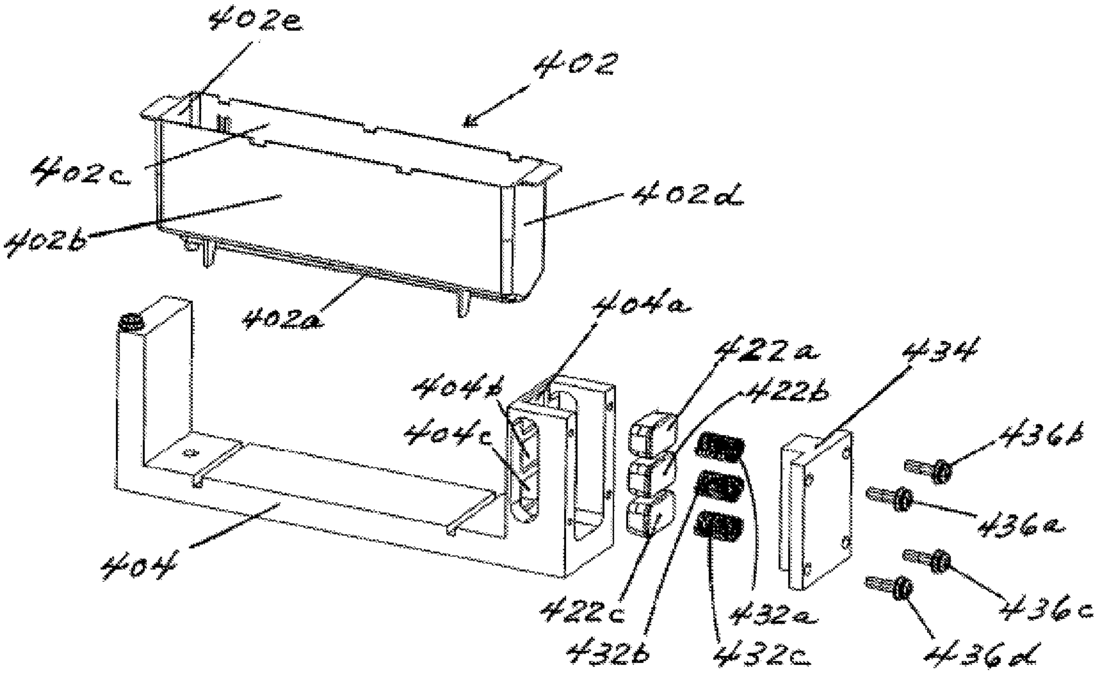
FIG. 14 is an exploded perspective view of the embodiment shown in FIG. 13.

The trough 402 does not have receptacles for receiving liquid level sensors. In this embodiment, shown in FIGS. 13 and 14, the holder 404 has three apertures 404 *a*, 404 *b* and 404 *c* formed in one end 404 *d* of the holder 404. Each aperture 404 *a*, 404 *b* and 404 *c* is capable of allowing a liquid level sensor 422 *a*, 422 *b*, and 422 *c*, respectively, to pass therethrough in order to enable the liquid level sensors 422 *a*, 422 *b*, and 422 *c* to be attached to the end wall 402 *d* of the trough 402. Attachment of the liquid level sensors 422 *a*, 422 *b*, and 422 *c* to the end wall 402 *d* of the trough can be effected by means of an adhesive. The liquid level sensors 422 *a*, 422 *b*, and 422 *c* are secured to the end wall 402 *d* of the trough 402 by means of an arrangement comprising springs 432 *a*, 432 *b*, and 432 *c*, which springs are held in place by a pressure plate 434. The pressure plate 434 is fastened to the end 404 *d* of the holder 404 by a set of bolts 436 *a*, 436 *b*, 436 *c*, and 436 *d*. The liquid level sensors 422 *a*, 422 *b*, and 422 *c* are of such a design that they do not require receptacles on the end 402 *d* of the trough 402 in order to function. Such liquid level sensors are commercially available from Moog, Inc., Salt Lake City, Utah under the designation Lifeguard™ Point Level Sensor. In this embodiment, a tube for filling the trough 402 is not shown. However, it should be apparent to one of ordinary skill in the art any of several ways to set up a tube for filling the trough 402.

Bulk liquids, such as, for example, a pre-trigger solution for certain types of immunoassays, wash buffer, and deionized water, are preferably contained in troughs, so that a plurality of pipette tips can aspirate a specific liquid simultaneously. The purpose of the pre-trigger solution is to enable the release of a chemiluminescent material, e.g., acridinium, from the conjugate that has bound to the magnetic microparticles in an immunoassay. In addition, the pre-trigger solution adds hydrogen peroxide and lowers the pH to a level so that no photons are emitted from the chemiluminescent material. A trigger solution complementary to the pre-trigger solution raises the pH back to neutral by means of a basic solution, e.g., sodium hydroxide solution, and allows the hydrogen peroxide to generate photons from the chemiluminescent material. Dispensing of bulk liquids can also be performed by a sub-system on the analysis section 10 in order to reduce the burden of the aspirating/dispensing device 92. As shown in FIGS. 1 and 2, the area 46 of the analysis section 10 can accommodate six (6) troughs. The number of troughs that can be accommodated by the area 46 of the analysis section 10 is not critical. The numbers set forth previously are merely representative examples for a typical arrangement. Other bulk liquids can be stored where appropriate. For example, the trigger solution for certain types of immunoassays, which is used in conjunction with the pre-trigger solution, can be stored in a reader, such as, for example, a luminescence reader, whereby the trigger solution is released at the point when the results of the assay are to be read. The trigger solution enables photons to be emitted from the label of the reaction product of the immunoassay within from about three (3) to about five (5) seconds.

To ensure that each bulk liquid is loaded into the correct location, a radio frequency identification antenna is positioned on the base of each container of bulk liquid. The radio frequency identification antenna can read the radio frequency identification tag attached to the base of each container. The recess receives and holds a container of bulk liquid, and, in addition, provides positive registration of the position of the container of bulk liquid. An antenna is located at bottom of the recess for each container for bulk liquid. When a container is loaded into a recess, the identity of the container can be verified by reading the radio frequency identification tag attached to the base of the container.

In addition, restrictive tubing lengths and divider walls between containers can be used to prevent bulk liquid straw assemblies from being inserted into incorrect containers of bulk liquids. By limiting the lengths of tubing and providing divider walls/recesses for each bulk liquid bottle, the appropriate straw assembly can be placed into the correct bottle only.

The bulk liquid handling software resides on a bulk liquid handling controller. The software operates in the following manner.

Power is applied to the sub-system, at which point the system boots up, runs a self test, initializes communication, sets all channels to INACTIVE, and waits for commands. The real time controller requests the current status of the sub-system.

The bulk liquid handling sub-system can report the status of each channel, but the volumes of bulk liquids remaining containers of bulk liquids are not reported for channels that were not initialized at a volume greater than zero in a container of bulk liquid upon receiving a RUN command. Each local reservoir is associated with a channel of the bulk liquid handling sub-system. The controller for the bulk liquid handling sub-system does not retain records of volumes of liquids in containers of bulk liquids after a shut-down of power. If a non-zero value for the level of a liquid in a container is not provided via a RUN command, the bulk liquid handling controller does not have any volume of liquid from which to subtract a value when a volume of liquid from a container of bulk liquid is consumed.

Based on the status of the bulk liquid handling sub-system, the real time controller may send a RUN command to the hulk liquid handling sub-system to maintain the level of liquid of each local reservoir at the proper level and to initialize volumes of liquids remaining in the containers of bulk liquids. When the bulk liquid handling controller receives a RUN command, the bulk liquid handling controller can begin controlling liquid level between the levels of low and full for each local reservoir, e.g., trough, commanded. In addition, the bulk liquid handling controller can subtract the value of the volume of liquid consumed from the value of the starting volume as liquids are consumed.

The real time controller can determine if an accessory, such as, for example, an ARCHITECT® Automatic Reconstitution Module, is present and send this information to the bulk liquid handling controller, along with starting volumes of liquid in all of the containers of bulk liquids.

When a container becomes empty, the bulk liquid handling controller can internally change the status of the container and disable the channel(s) affected.

The bulk liquid handling controller can determine that the container of bulk liquid is empty by timing the fill operation to move the level of liquid from low to full in a local reservoir, e.g., a trough. If the expected filling time is exceeded and the level of liquid in the bulk container is below the low sensor, the bulk liquid handling sub-system can interpret this measurement to mean that the container of bulk liquid is empty.

Periodically, the real time controller can request the status of the bulk liquid handling sub-system from the bulk liquid handling controller. The real time controller can interpret the status returned from the bulk liquid handling controller and determine whether a container of bulk liquid is empty. Then, the real time controller can instruct the operator to replace the container of bulk liquid. The real time controller can send a RUN command, with the value of the new starting volume of the container of bulk liquid, indicating that the fault, i.e., empty container of bulk liquid, has been corrected. A fault message disables a channel.

The bulk liquid handling controller can check to determine whether the liquid level sensor for the container of bulk liquid was reconnected and whether the low sensor for the container of bulk liquid is activated (i.e., the container is not empty; the container contains a minimum amount of liquid) before re-enabling the previously disabled channels and continuing to maintain the levels of liquid.

The real time controller can send a STOP command along with specific identifiers for various channels. The real time controller can instruct the operator to insert all connections of the containers of bulk liquid into one container of bulk liquid that contains a cleaning solution. The real time controller can send a CLEAN command for the specific channels that need to be cleaned or replaced. The bulk liquid handling sub-system can fill the specific local reservoirs, e.g., troughs, with the cleaning solution up to the low sensor level and then stop. The real time controller can then wait to allow the liquid lines to soak and then send a DRAIN command identifying the specific channels to drain. The bulk liquid handling sub-system can completely empty the specific local reservoirs, e.g., troughs, so identified. The real time controller can instruct the operator to insert all connections for containers of bulk liquids into one container containing deionized water. The real time controller can send a CLEAN command for the specific channels that need to be cleaned or replaced. The bulk liquid handling sub-system can fill the local reservoirs, e.g., troughs, with deionized water up to the low level sensor and then stop. The real time controller can then wait to allow the liquid lines to soak and then send a DRAIN command to the channels specified. The bulk liquid handling sub-system can completely empty the specific local reservoirs, troughs. The real time controller can repeat cleaning with deionized water as many tithes as specified.

The real time controller can instruct the operator to re-insert the connections to the containers into the original containers of bulk liquids. The real time controller can instruct the operator to disengage the sensors and liquid connections from the local reservoirs, e.g., troughs, and dispose of the local reservoirs, e.g., troughs. The real tinge controller can instruct the operator to replace the local reservoirs, e.g., troughs, and to engage the liquid level sensors and liquid connections. The bulk liquid handling controller manages pumps and valves (if the valves are electronic) to drain local reservoirs to a waste container or to a drain.

During draining, if the waste container becomes full, the bulk liquid handling controller can internally change the status of the channels and disable the channels that require removal of waste. Periodically, the real time controller can request the status of the bulk liquid handling sub-system from the bulk liquid handling controller. The real time controller can interpret the status of the bulk liquid handling sub-system returned from the bulk liquid handling controller and determine whether the waste container is full. The real time controller can instruct the operator to empty the waste container. The real time controller can also send a DRAIN command to the bulk handling controller, indicating that the fault was corrected.

The bulk liquid handling controller can check to determine whether the waste sensor has been reconnected and whether the waste container is still not full before continuing to drain the local reservoirs, e.g., troughs.

The bulk liquid handling sub-system maintains the level of liquids in the various local reservoirs, e.g., troughs. The bulk liquid handling sub-system prevents overflows from the local reservoirs, e.g., troughs. The real time controller enables the aspirating/dispensing device to access the troughs. The bulk liquid handling controller allows the level of liquid in the local reservoirs, e.g., troughs, to be maintained without interaction from a real time controller. The bulk liquid handling controller tracks the volume of liquid remaining in the containers of bulk liquids. The bulk liquid handling sub-system allows an operator continuous access to replace containers of bulk liquids. The bulk liquid handling sub-system eliminates the need to prime channels after containers containing bulk liquids are replaced. The bulk liquid handling sub-system allows for disposal of local reservoirs, e.g., troughs, at specified intervals. The bulk liquid handling sub-system handles removal of liquid waste. The bulk liquid handling sub-system provides access to optional accessories, such as, for example, the ARCHITECT® Automatic Reconstitution Module. The bulk liquid handling sub-system provides the capability to clean local reservoirs, e.g., troughs. The bulk liquid handling sub-system allows each channel to be operated independently. For example, a first channel can be maintaining the level of liquid in a given trough while a second is being cleaned with a cleaning solution.

Various modifications and alterations of this disclosure will become apparent to those skilled in the art without departing from the scope and spirit of this disclosure, and it should be understood that this disclosure is not to be unduly limited to the illustrative embodiments set forth herein.

What is claimed is:

1. A method comprising:

sensing a level of a bulk liquid in a first container disposed in an automated diagnostic analyzer;

automatically pumping, via a pump, a volume of the bulk liquid from a second container storing the bulk liquid to the first container when the level of the bulk liquid in the first container is below a threshold, the second container being fluidly coupled to the first container via a fluid conduit, and the pump coupled to the fluid conduit;

transferring a first portion of the bulk liquid from the first container to a first aspirating/dispensing device; and dispensing, via the first aspirating/dispensing device, the first portion of the bulk liquid into a reaction vessel.

2. The method of claim 1 further comprising:

transferring a second portion of the bulk liquid from the first container to a second aspirating/dispensing device simultaneously as the first portion of the bulk liquid is transferred to the first aspirating/dispensing device; and dispensing, via the second aspirating/dispensing device, the second portion of the bulk liquid.

3. The method of claim 1, wherein the reaction vessel is disposed within a kitting area of the automated diagnostic analyzer, the kitting area being located above the second container.

4. The method of claim 1 further comprising instructing, via a controller, an operator to replace the second container with a third container having the bulk liquid and pumping the bulk liquid from the third container to the first container when the level of the bulk liquid in the first container is below the threshold.

5. The method of claim 1, wherein the sensing is performed via a capacitive sensor coupled to an outer surface of the first container.

6. The method of claim 1, wherein the first container comprises a trough having an open top.

7. The method of claim 1 further comprising:

operating, via a controller, a valve to transfer the bulk liquid from the first container to a waste container or drain.

8. The method of claim 1 further comprising pumping the volume of bulk liquid through a valve coupled to the fluid conduit.

9. The method of claim 8 further comprising operating, via a controller, the valve to transfer the volume of bulk liquid to the first container.

10. The method of claim 8, wherein the valve is a check valve.

11. The method of claim 7, wherein the reaction vessel is disposed within a kitting area of the automated diagnostic analyzer, the kitting area being located above the waste container.

12. The method of claim 7, wherein sensing the level of the bulk liquid in the first container comprises sensing the level of the bulk liquid via a sensor coupled to an outside of the first container.

13. The method of claim 12, wherein the sensor comprises three sensors, including a low level sensor to indicate when the bulk liquid is at or below a low threshold of a capacity of the first container, a full level sensor to indicate when the bulk liquid is at or above a high threshold of the capacity of the first container and an overfill sensor to indicate when the bulk liquid is at or near 100% of the capacity of the first container.

14. The method of claim 12, wherein the sensor is a capacitive sensor.

15. The method of claim 7, wherein the first container comprises a trough having an open top.

* * * * *